United States Patent
Brown et al.

(10) Patent No.: US 11,441,197 B2
(45) Date of Patent: Sep. 13, 2022

(54) IN SILICO DESIGN OF MAMMALIAN PROMOTERS WITH USER-DEFINED FUNCTIONALITY

(71) Applicant: MEDIMMUNE LIMITED, Cambridge (GB)

(72) Inventors: Adam J. Brown, Sheffield (GB); David C. James, Sheffield (GB); Suzanne J. Gibson, Cambridge (GB); Diane Hatton, Cambridge (GB)

(73) Assignee: MedImmune Limited, Cambridge (GB)

( * ) Notice: Subject to any disclaimer, the term of this patent is extended or adjusted under 35 U.S.C. 154(b) by 270 days.

(21) Appl. No.: 16/605,308

(22) PCT Filed: Apr. 19, 2018

(86) PCT No.: PCT/EP2018/060125
§ 371 (c)(1),
(2) Date: Oct. 15, 2019

(87) PCT Pub. No.: WO2018/193072
PCT Pub. Date: Oct. 25, 2018

(65) Prior Publication Data
US 2021/0147951 A1    May 20, 2021

Related U.S. Application Data

(60) Provisional application No. 62/487,017, filed on Apr. 19, 2017.

(51) Int. Cl.
C07H 21/02 (2006.01)
C12Q 1/6897 (2018.01)
C12N 15/10 (2006.01)

(52) U.S. Cl.
CPC ....... *C12Q 1/6897* (2013.01); *C12N 15/1086* (2013.01); *C12Q 2525/143* (2013.01); *C12Q 2525/197* (2013.01)

(58) Field of Classification Search
USPC ...... 435/6.1, 6.11, 320.1; 436/501; 536/23.1
See application file for complete search history.

(56) References Cited

U.S. PATENT DOCUMENTS

2003/0082648 A1* 5/2003 Hinuma ............... C07K 14/705
435/7.21

FOREIGN PATENT DOCUMENTS

| WO | WO 2015/079053 A2 | 6/2015 |
| WO | WO 2015/111024 A1 | 7/2015 |

OTHER PUBLICATIONS

Schulthess et al., Signal integration by the CYP1A1 promoter—a quantitative study. Nucleic Acids Research, 43, 5318-5330, 2015.*
Weingarten-Gabbay et al., The grammar of transcriptional regulation. Hum. Genet., 133, 701-711, 2014.*
"plasmid: pT81luc". Printed on Nov. 19, 2021.*
Smith, R., et.al, "Massively parallel decoding of mammalian regulatory sequences supports a flexible organizational model," Nature Genetics, vol. 45, No. 9, Jul. 28, 2013, pp. 1021-1028.

* cited by examiner

*Primary Examiner* — Frank W Lu

(57) ABSTRACT

As demonstrated herein, when composite transcription factor binding sites do not function synergistically, mammalian promoters can be constructed according to simple design rules. Host-cell transcriptional machinery components were analyzed in silico to identify transcription factors with desired expression dynamics. Cognate binding sites were then comprehensively tested in homotypic and heterotypic architectures to assess modularity and determine the transcriptional activity exhibited by a single copy of each site. When elements were specifically selected to prevent combinatorial interactions, heterotypic promoter activities could be accurately modeled simply as a function of constituent binding site copy numbers. As binding site order, spacing, and orientation had minimal effect on promoter activity, blocks could be optimally combined and arranged in silico according to context-specific design-criteria. To demonstrate this, CHO cell promoters were created de-novo that exhibited designed activity levels and long-term expression stability in vitro.

1 Claim, 8 Drawing Sheets

Figure 1:
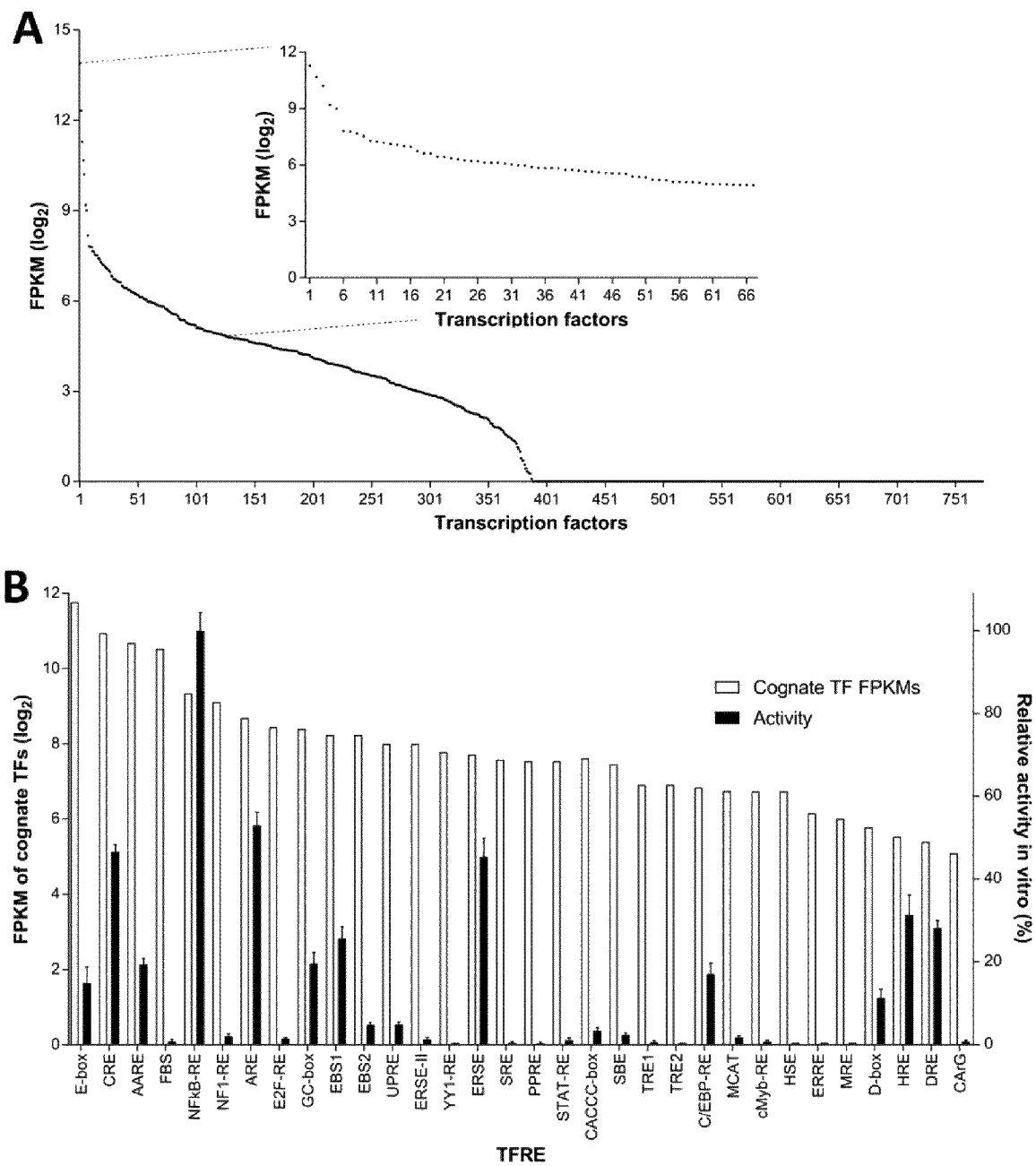

Specification includes a Sequence Listing.

IN SILICO DESIGN OF MAMMALIAN PROMOTERS WITH USER-DEFINED FUNCTIONALITY

CROSS-REFERENCE TO RELATED APPLICATIONS

This application is a U.S. National Stage application of International Application No. PCT/EP2018/060125, filed on Apr. 19, 2018, said International Application No. PCT/EP2018/060125 claims benefit under 35 U.S.C. § 119(e) of the U.S. Provisional Application No. 62/487,017, filed Apr. 19, 2017. Each of the above listed applications is incorporated by reference herein in its entirety for all purposes.

REFERENCE TO THE SEQUENCE LISTING

This application incorporates by reference a Sequence Listing submitted with this application as text file entitled SYNPRO-100-WO-SL.TXT, created on Oct. 14, 2019, and having a size 12,462 of kilobytes.

BACKGROUND

Context-specific promoter-performance is a function of promoter activity dynamics, long-term gene expression cassette behaviour (e.g. propensity for silencing, compatibility with other genetic components (1)), and promoter-cell interactions (e.g. off-target effects on cellular processes, for example by sequestration of transcriptional machinery components (2,3)). Given the inherent limitations of naturally-evolved sequences, for example undesirable sizes and unpredictable expression dynamics, synthetic promoters are typically preferred for most applications. The simplest method of synthetic promoter construction involves enhancing the function of existing promoters by removing (4,5), inserting (6,7), or mutating (8,9) sequence elements (for a comprehensive review of synthetic promoter construction methods see (10)). However, whilst this strategy enables incremental improvements in endogenous/viral promoter performance, it is unlikely that sub-optimal starting-sequences can be fully optimized-for-function via re-engineering. In contrast, the bottom-up construction of completely synthetic constructs enables a massive expansion of the promoter design space.

Entirely synthetic systems, comprising synthetic transcription factors (i.e. zinc finger (11), transcription activator-like effector (12), chimeric (13), and CRISPR-transcription factors (14)) that trans-activate synthetic promoters containing their cognate binding sites (transcription factor regulatory elements (TFREs)), impose minimal host cell-promoter interactions. However, the associated metabolic burden and introduction of other exogenous recombinant protein(s) may limit the attractiveness of these systems in some applications, such as gene therapy and biopharmaceutical production. Constructing artificial promoters that interact with the host cell's existing repertoire of transcription factors (TFs) obviates the requirement for accessory TFs, but the synthetic promoter-endogenous TF-endogenous promoter interactome can negatively affect the activity dynamics of both synthetic and endogenous promoters (2,3,15). Accordingly, using currently available promoter construction methods, it is challenging to optimize promoter, expression cassette and host-cell performance simultaneously. Concurrent optimization of these interrelated functionalities may only be possible via custom-design of promoters (that do not require complementary synthetic TFs) in silico. Indeed, a move towards de novo synthetic design of genetic parts is a key objective for mammalian synthetic biology.

In silico promoter design is limited by the complex rules that govern promoter activity, including the orientation, spatial positioning, and order of composite TFREs, and the function, expression level, and activity of their cognate TFs (16,17). However, Smith et al. recently systematically tested the rules of TFRE organization in thousands of artificial sequences, and found that promoter activities were predominantly simply a function of relative TFRE copy numbers (18). These findings support the billboard model of TFRE organisation, where binding site spacing, order, and orientation can be largely disregarded (19,20). However, in the promoters constructed by Smith et al. (18) activities were impacted by combinatorial interactions between various TFRE-pairs. When composite TFREs are capable of synergistic and/or interfering interactions, relative TFRE order can significantly impact promoter activity, substantially increasing the complexity of in silico promoter design. However, studies have shown that combinatorial interactions between TFs are relatively uncommon (21). Moreover, Smith et al. only identified eight (out of a possible sixty-six) combinatorial TFRE interactions amongst the twelve TFREs that were used for promoter construction (18). Methods of selecting TFREs that do not function cooperatively in order to build promoters with relatively simple design rules are needed.

BRIEF SUMMARY OF THE INVENTION

The methods provided herein demonstrate that it is possible to specifically select combinations of modular TFREs that do not function cooperatively, and utilize them to build promoters with relatively simple design rules. Given that TF concentration levels correlate well with cognate binding site activities (22,23), it was hypothesized that in silico promoter design could be achieved by i) profiling TF expression in the host cell, ii) identifying TFREs that do not function synergistically, and iii) determining the relative transcriptional activity of TF-TFRE interactions within heterotypic elements (i.e. the contribution to overall promoter activity provided by a single copy of each TFRE). By applying this measure-model-manipulate paradigm, this study, for the first time, reports model-directed design of synthetic promoters in silico that exhibit designed functionalities in vitro. A simplified model of heterotypic promoter activities enabled de-novo design of synthetic elements, where the composition and order of modular TFRE-blocks could be optimized according to context-specific requirements such as long-term expression stability and desired activity dynamics. By demonstrating that promoters can be synthetically designed according to simple design rules, this study reveals new insights into eukaryotic transcriptional regulatory mechanisms, and provides key enabling tools for mammalian synthetic biology.

Accordingly, provided herein are synthetic promoters. In one aspect, a synthetic promoter comprises (a) a nucleotide sequence comprising 4 to 20 transcription factor regulatory elements (TFREs) and (b) a promoter core, wherein the nucleotide sequence comprising the TRFEs is upstream of the promoter core, and wherein at least one third of the TFREs are individually selected from the group consisting of antioxidant RE (ARE), ETS binding site 1 (EBS1), endoplasmic reticulum stress RE (ERSE), and dioxin RE (DRE) TFREs. In one aspect, the nucleotide sequence comprises spacers between the TFREs, wherein the spacers are no more than 50 nucleotides, no more than 25 nucleotides, or no more than 12 nucleotides. In one aspect, the spacers are about 6 nucleotides. In one aspect, the core promoter is a CMV core promoter, optionally wherein the CMV core promoter comprises the nucleotide sequence of SEQ ID NO:33.

As provided herein, a synthetic promoter can comprise the nucleotide sequence of any one of SEQ ID NOs:37-50.

Also provided herein are methods of designing a synthetic promoter. In one aspect, a method of designing a synthetic promoter comprises: (i) profiling transcription factor (TF) expression to select TFs, (ii) identifying transcription factor regulatory elements (TFREs) that interact with the selected TFs that are transcriptionally active in a homotypic promoter, and (iii) determining the relative transcriptional activity of TF-TFRE interactions within a heterotypic promoter. In one aspect, the method further comprises (iv) selecting TFREs with a desired transcriptional activity. In one aspect, the method further comprises (v) producing a synthetic promoter comprising (a) a nucleotide sequence comprising the selected TFREs with the desired transcriptional activity and (b) a promoter core, wherein the nucleotide sequence comprising the TRFEs is upstream of the promoter core.

In one aspect, the profiling TF expression comprises determining the abundance of the TFs. In one aspect, the determining the abundance of the TFs comprises measuring the RNA or protein level of the TFs. In one aspect, the profiling TF expression comprises profiling TF expression in at least two cell types. In one aspect, the at least two cell types are mammalian cell types. In one aspect, the at least two mammalian cell types are CHO cells. In one aspect, the at least two cell lines comprise a cell line expressing a recombinant protein and its parent cell line. In one aspect, the at least two cell types are two cell types from the same organism, optionally wherein the organism is a human.

In one aspect, TFs that are highly expressed are selected. In one aspect, TFs with expression levels within the top 50%, 45%, 40%, 35%, 30%, 25%, 20%, 15%, or 10% are selected.

In one aspect, the profiling TF expression comprises determining the stability of TFs across at least two cell types, at least two phases of cell culture, and/or at least two culture conditions. In one aspect, the method further comprises selecting TFs with a maximum fold change of less than or equal to 2, or 1.5, or 1 in expression levels across the at least two cell types, at least two phases of cell culture, and/or at least two culture conditions.

In one aspect, the profiling TF expression comprises profiling TF expression in at least two phases of cell culture. In one aspect, the at least two phases of cell culture comprise a stationary phase and an exponential growth phase. In one aspect, TFs that are preferentially upregulated in an intended host cell and/or preferentially down-regulated in an off-target host cell are selected. In one aspect, TFs that are preferentially upregulated in an intended cell-cycle phase and/or down-regulated in an off-target cell-cycle phase are selected.

In one aspect, the expression of at least 100 TFs is profiled.

In one aspect, the homotypic promoter comprises 2 to 20 copies of a TFRE. In one aspect, the homotypic promoter comprises 4 to 10 copies of a TFRE.

In one aspect, the determining the relative transcriptional activity comprises modeling the heterotypic promoter activity as a function of TFRE copy number. In one aspect, the heterotypic promoter comprises 2 to 20 TFRE.

Also provided herein is a synthetic promoter produced according to a method provided herein. In one aspect, the synthetic promoter comprises a nucleotide sequence comprising 4 to 20 TFREs and a promoter core, wherein the nucleotide sequence comprising the TRFEs is upstream of the promoter core. In one aspect, at least one TFRE is selected from the group consisting of antioxidant RE (ARE), ETS binding site 1 (EBS1), endoplasmic reticulum stress RE (ERSE), and dioxin RE (DRE) TFREs. In one aspect, the nucleotide sequence comprises spacers between the TFREs, wherein the spacers are no more than 50 nucleotides, no more than 25 nucleotides, or no more than 12 nucleotides. In one aspect, the spacers are about 6 nucleotides. In one aspect, the core promoter is a CMV core promoter, optionally wherein the CMV core promoter comprises the nucleotide sequence of SEQ ID NO:33.

In one aspect of a promoter provided herein and/or produced according to a method provided herein, the nucleotide sequence comprising the TFREs comprises no more than 10 CpG dinucleotides. In one aspect, the nucleotide sequence comprising the TFREs comprises no more than 5 CpG dinucleotides In one aspect, the nucleotide sequence comprising the TFREs does not contain any repeat sequences greater than 20 nucleotides in length. In one aspect, the nucleotide sequence comprising the TFREs does not contain any EcoRI, BamHI, HindIII, TaqI, NotI, SmaI, PvuI, or PacI restriction endonuclease sites. In one aspect, the nucleotide sequence comprising the TFREs does not contain any EcoRI, BamHI, HindIII, TaqI, NotI, SmaI, PvuI, PacI, XhoI, or KpnI restriction endonuclease sites. In one aspect, the order of the TFREs does not significantly influence the activity of the synthetic promoter.

In one aspect, the orientation of the TFREs does not significantly influence the activity of the synthetic promoter. In one aspect, the activity of the promoter correlates with the number of copies of each TFRE.

In one aspect, the synthetic promoter does not have a significant effect on cell growth. In one aspect, the synthetic promoter does not have a significant effect on cell viability. In one aspect, the synthetic promoter does not contain a TFRE that is transcriptionally inactive in a heterotypic promoter. In one aspect, the synthetic promoter does not contain a TFRE that is transcriptionally repressive in a heterotypic promoter.

In one aspect, the ARE TFRE comprises the nucleotide sequence of SEQ ID NO:7. In one aspect, the EBS1 TFRE comprises the nucleotide sequence of SEQ ID NO:10. In one aspect, the ERSE TFRE comprises the nucleotide sequence of SEQ ID NO:15. In one aspect, the DRE TFRE comprises the nucleotide sequence of SEQ ID NO:31.

In one aspect, the synthetic promoter further comprises additional CHO cell TFREs. In one aspect, at least one of the additional CHO cell TFREs comprises the nucleotide sequence of any one of SEQ ID NOs:6, 9, and 23.

In one aspect, the nucleotide sequence comprising TFREs comprises at least 2 copies of the same TRFE. In one aspect, the nucleotide sequence comprising TFREs comprises at least 3 copies of the same TRFE.

In one aspect, the synthetic promoter avoids promoter silencing. In one aspect, the synthetic promoters minimizes off-target effects on key cellular processes that underpin protein production.

Also provided herein is a vector comprising a synthetic promoter provided herein. In one aspect, the synthetic promoter of the vector is operably linked to a gene encoding a protein. In one aspect, the protein is a reporter protein, therapeutic protein, or an enzyme.

Also provided herein is a cell comprising a synthetic promoter provided herein or a vector provided herein. In one aspect, the cell is a mammalian cell. In one aspect, the mammalian cell is a CHO cell. In one aspect, the mammalian cell is a human cell.

Also provided herein is a library comprising synthetic promoters provided herein. In one aspect, the library comprises at least 100 different synthetic promoters.

BRIEF DESCRIPTION OF THE DRAWINGS/FIGURES

FIGS. 1A and 1B: Identification of modular, transcriptionally active TFREs that bind relatively abundant host-cell components. FIG. 1A) RNA-seq analysis of CHO cell transcriptomes determined the relative expression level of host-cell transcription factors (TFs). Points represent the average expression level of each TF in three discrete CHO cell lines, sampled at exponential and stationary phases of culture (n=6). Inset graph shows the expression level of 67 TFs that exhibit high (ranked in the top 30% of TF mRNA expression levels) and stable expression across different CHO cell lines and growth phases (maximum fold change <1.5). FPKM=fragments per kilobase of transcript per million fragments mapped. FIG. 1B) Cognate binding sites of TFs with appropriate expression dynamics were identified and cloned in series (6× copies) upstream of a minimal CMV core promoter in SEAP-reporter vectors. CHO cells were transiently transfected with each TFRE-reporter and SEAP activity was measured 24 h post-transfection. Data are expressed as a percentage of the production exhibited by the strongest homotypic promoter. Bars represent the mean+SD of three independent experiments each performed in triplicate.

FIGS. 2A and 2B: Heterotypic assemblies of modular TFRE blocks exhibit transcriptional activities spanning over two orders of magnitude. FIG. 2A) TFREs that were transcriptionally active in homotypic architectures (see FIG. 1) were combined together in varying combinations to construct libraries of heterotypic promoters. Approximately twenty constructs were created within each library, where the order, orientation, spatial positioning and copy number of composite-TFREs was varied. FIG. 2B) Heterotypic elements were inserted upstream of a minimal CMV core promoter in SEAP reporter vectors and transiently transfected into CHO cells. SEAP expression was quantified 24 h post-transfection. Data are expressed as a percentage of the production exhibited by the strongest heterotypic promoter. SEAP production from the control hCMV-IE1-SEAP reporter is shown as the horizontal black line ("CMV"). Each bar represents the mean of two transfections; for each promoter, less than 10% variation in SEAP production was observed. Quantitative PCR (qPCR) analysis of SEAP transcript abundance confirmed that relative protein activities in cell culture supernatants were linearly correlated with SEAP mRNA levels (see FIG. 6).

Figure 2:
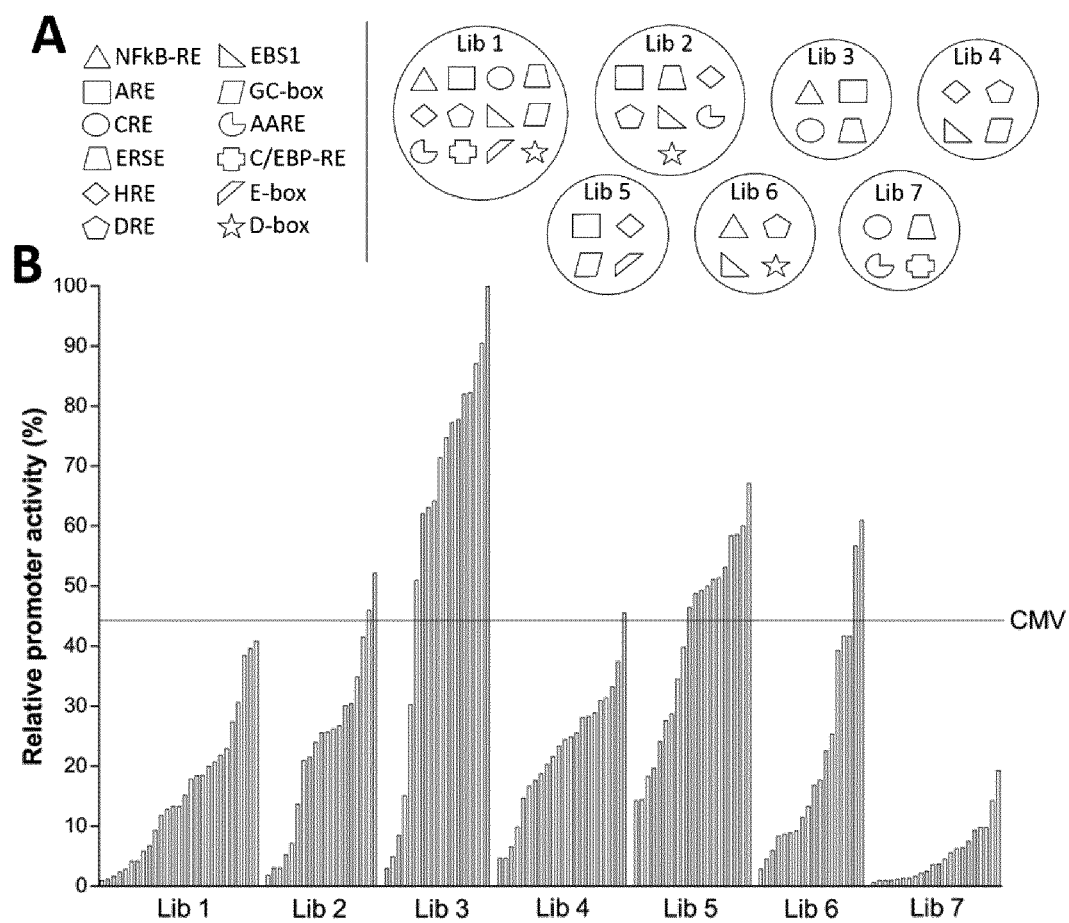
Figure 3:
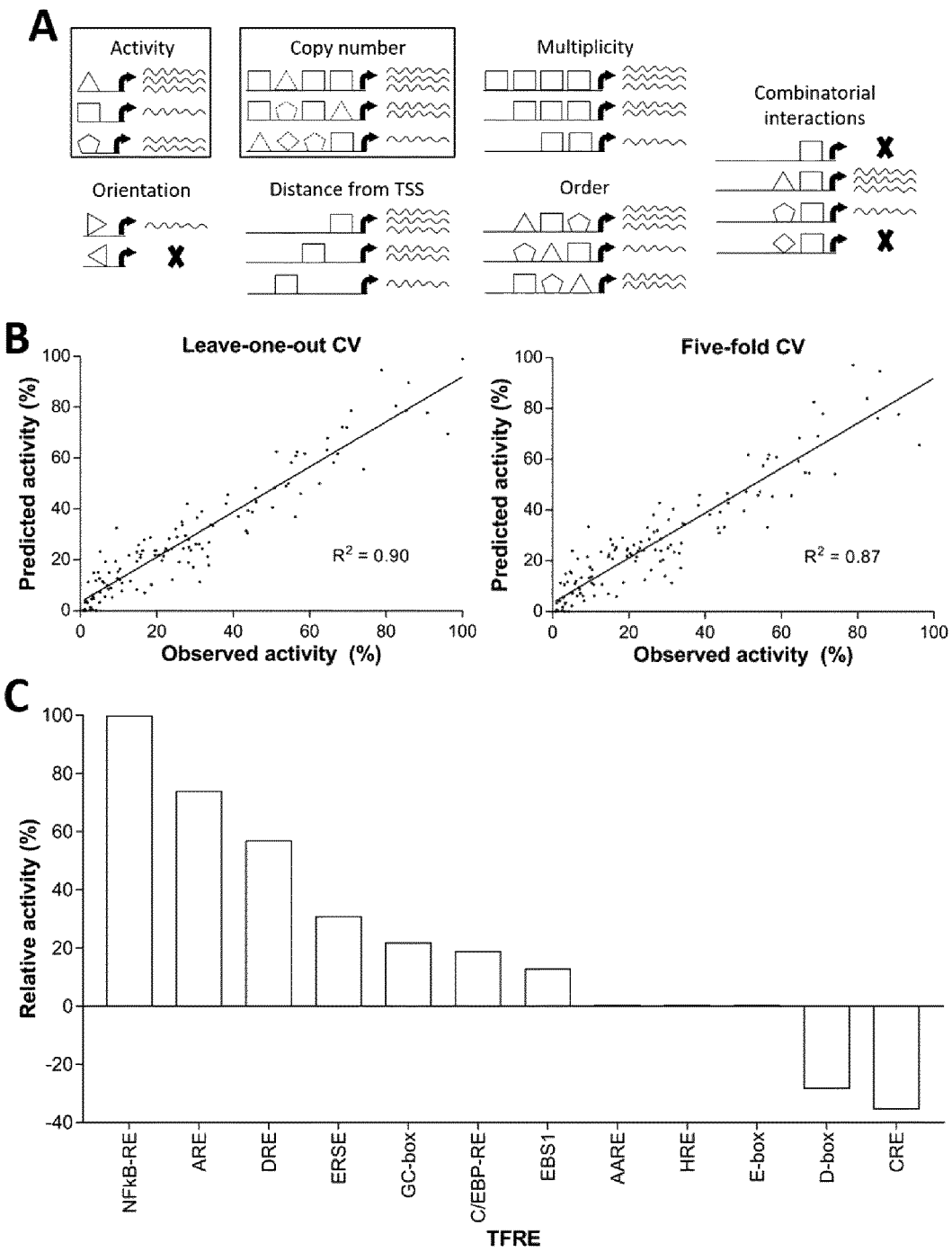

FIGS. 3A, 3B, and 3C. The function of modular TFRE-blocks in heterotypic promoter architectures is independent of binding site order and spacing. FIG. 3A) The function of discrete TFREs within heterotypic elements can be influenced by multiple 'rules'. We modeled heterotypic promoter activities (see FIG. 2) using TFRE copy numbers as the only predictor variables. FIG. 3B) The linear regression model's predictive power was analyzed using leave-one-out and five-fold cross validations (CV). FIG. 3C) The relative transcriptional activity of a single copy of each modular TFRE-block within heterotypic promoters was determined by analyzing the model coefficients.

Figure 4:
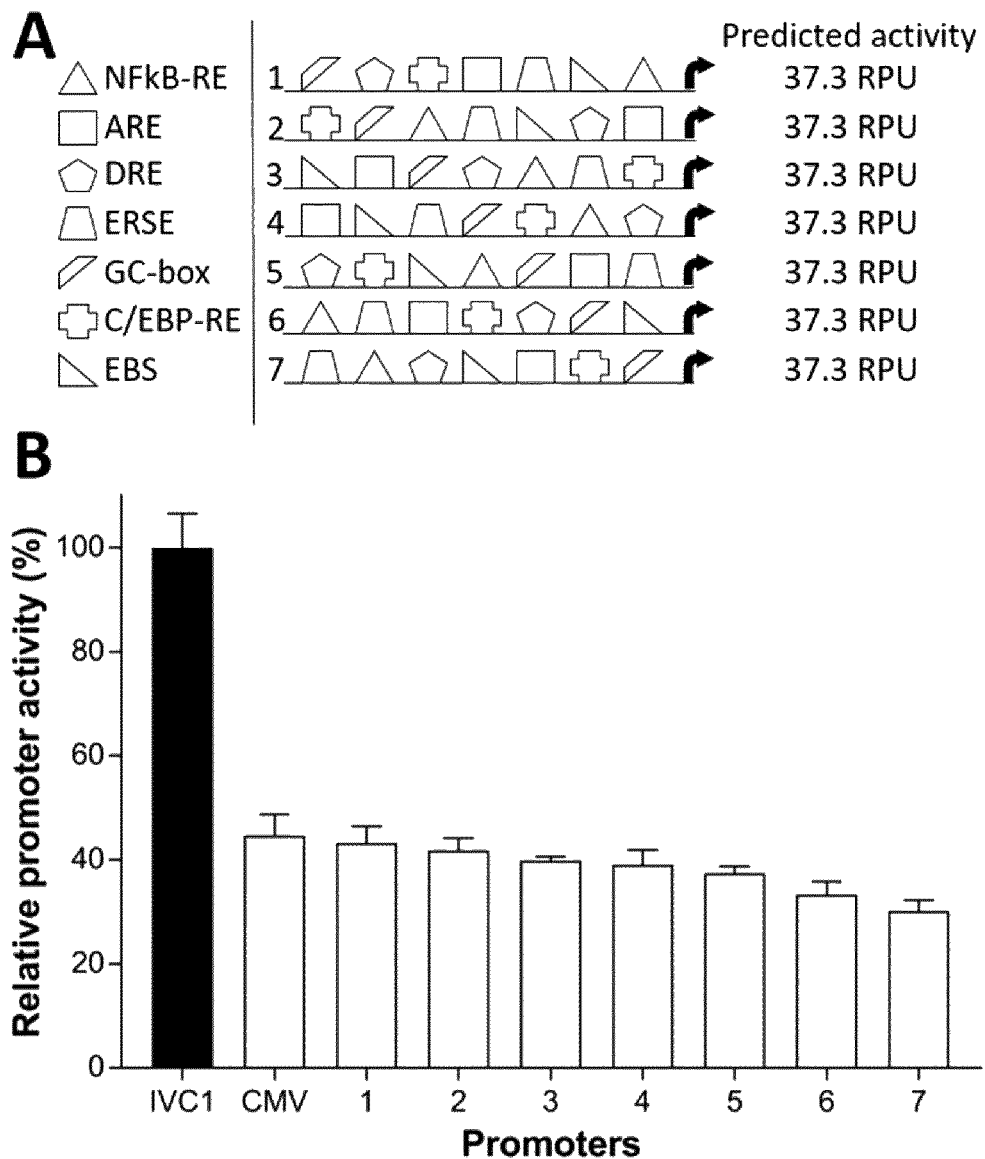

FIGS. 4A and 4B. Synthetically designed promoters exhibit predictable activities in vitro. FIG. 4A) Promoters with identical TFRE-compositions, but varying TFRE-orders, were designed in silico. The in vitro activity of each synthetic element was predicted using our model of heterotypic promoter activities (see FIG. 3). FIG. 4B) Synthetic promoters were chemically synthesized, inserted upstream of a minimal CMV core element in SEAP reporter vectors, and transiently transfected into CHO cells. SEAP expression was quantified 24 h post-transfection. Data are expressed as a percentage of the production exhibited by the strongest in vitro-constructed heterotypic promoter, IVC1 (equivalent to 100 relative promoter units (RPU); see FIG. 2). Values represent the mean+SD of three independent experiments performed in triplicate.

Figure 5:
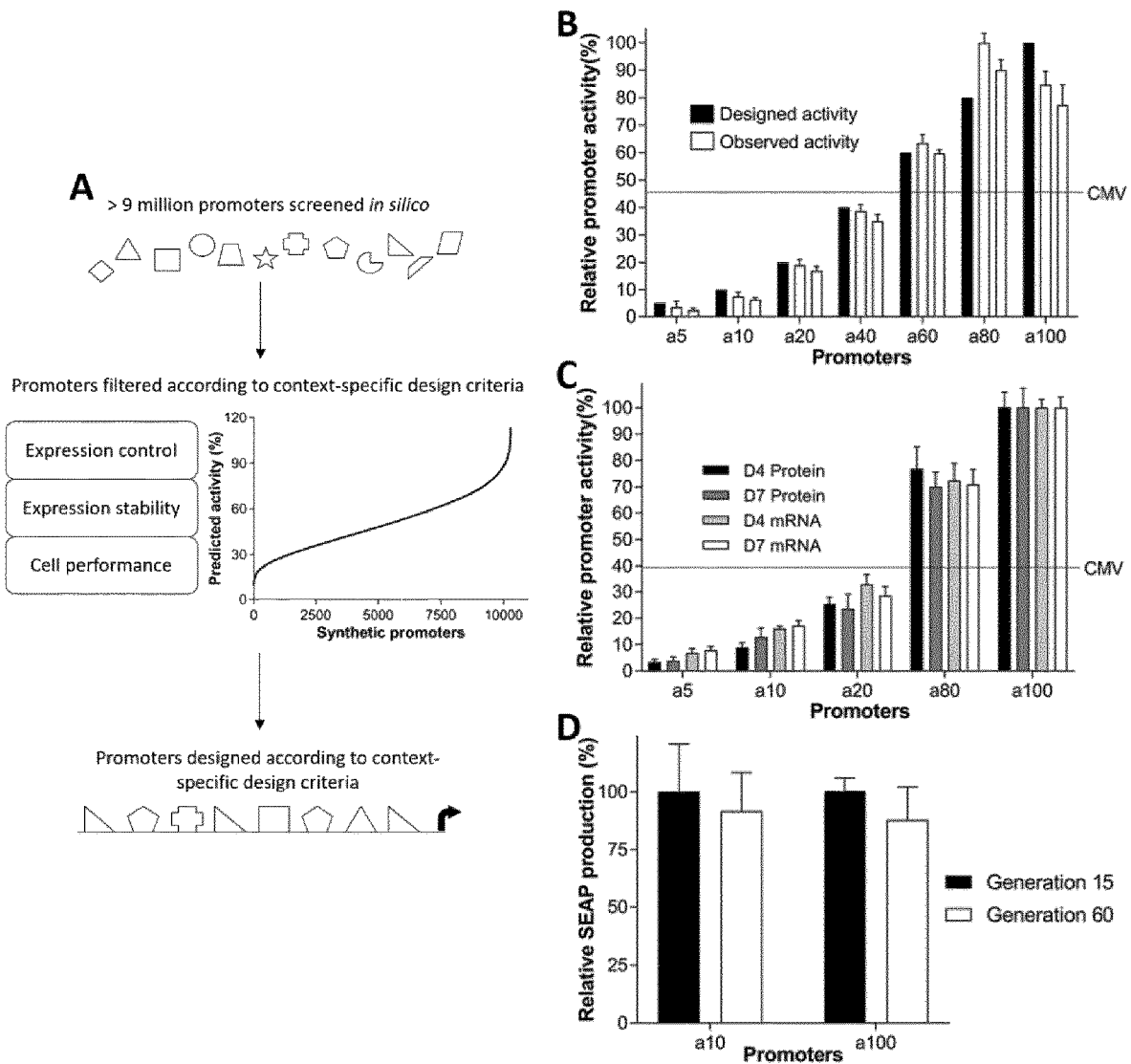

FIGS. 5A, 5B, 5C, and 5D. In silico designed sequences exhibit custom-defined functionalities in vitro. FIG. 5A) Millions of TFRE-combinations were constructed and tested in silico using our model of heterotypic element activities (see FIG. 3). Selection criteria were applied to identify combinations optimal for the context of biopharmaceutical production in CHO cells. Constituent TFREs within each promoter were then specifically arranged to prevent occurrences of sequence features that can contribute to promoter silencing. FIG. 5B) Synthetic promoters with varying designed activities were chemically synthesized, inserted upstream of a minimal CMV core element in SEAP-reporter vectors, and transiently transfected into CHO cells. SEAP expression was quantified 24 h post-transfection. Data are expressed as a percentage of the production exhibited by the strongest promoter. FIG. 5C) CHO cells were stably transfected with synthetic promoter-reporter plasmids coexpressing a glutamine synthetase selection marker gene. Following selection in medium containing methionine sulfoximine, promoter activities were measured during a 7-day batch-production process. SEAP titer and mRNA abundance were determined in mid-exponential and stationary phases of growth. Data are expressed as a percentage of the expression exhibited by the strongest promoter. FIG. 5D) Stable pools were subcultured in selective medium for sixty generations. SEAP expression was quantified at the end of a 7-day batch-production process. Data are expressed as a percentage of the production exhibited by each pool at generation fifteen. Values represent the mean+SD of three independent experiments performed in triplicate.

Figure 6:
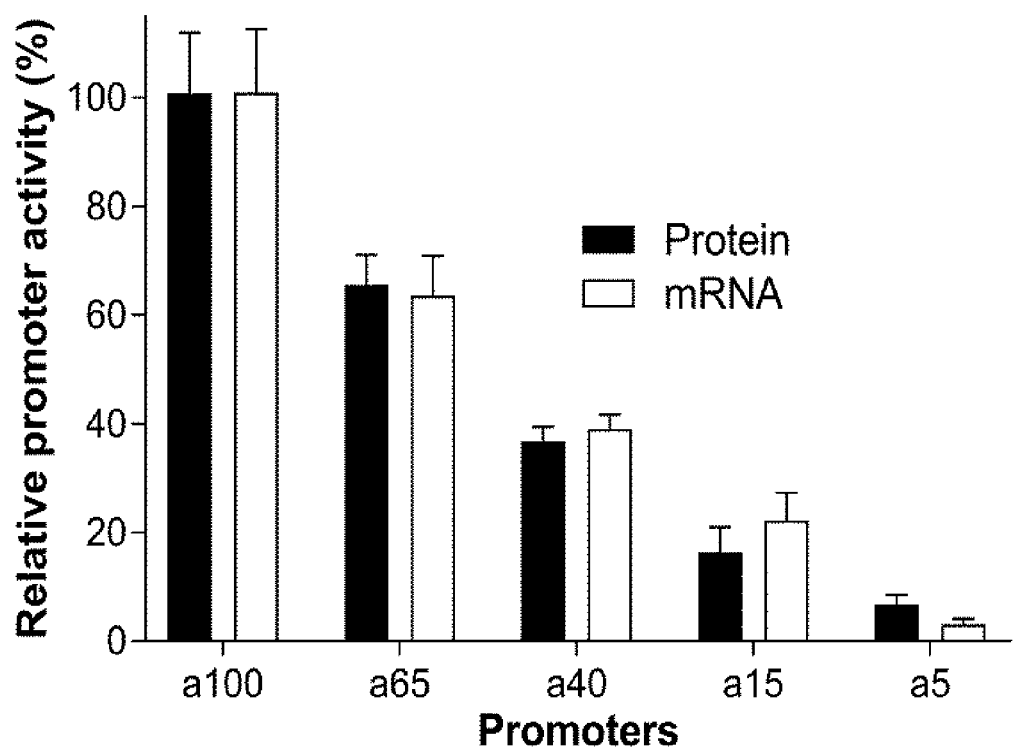

FIG. 6: SEAP activities in cell culture supernatants were linearly correlated with SEAP mRNA levels. In vitro-constructed heterotypic promoters were inserted upstream of a minimal CMV core promoter in SEAP reporter vectors and transiently transfected into CHO cells (see FIG. 2). SEAP expression was quantified 24 h post-transfection. Data are expressed as a percentage of the production exhibited by the strongest heterotypic promoter. Bars represent the mean+SD of three independent experiments each performed in triplicate.

Figure 7:
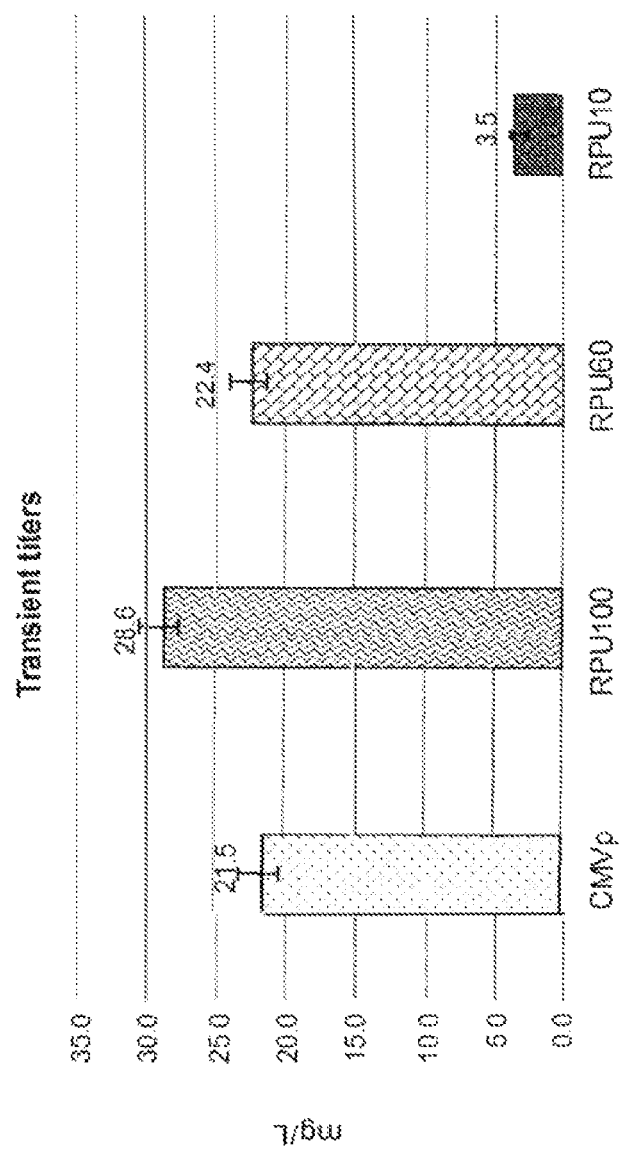

FIG. 7: Transient transfection titers. The expression levels of an immune activator protein under the control of various promoters is shown after transient transfections in CHO cells.

Figure 8:
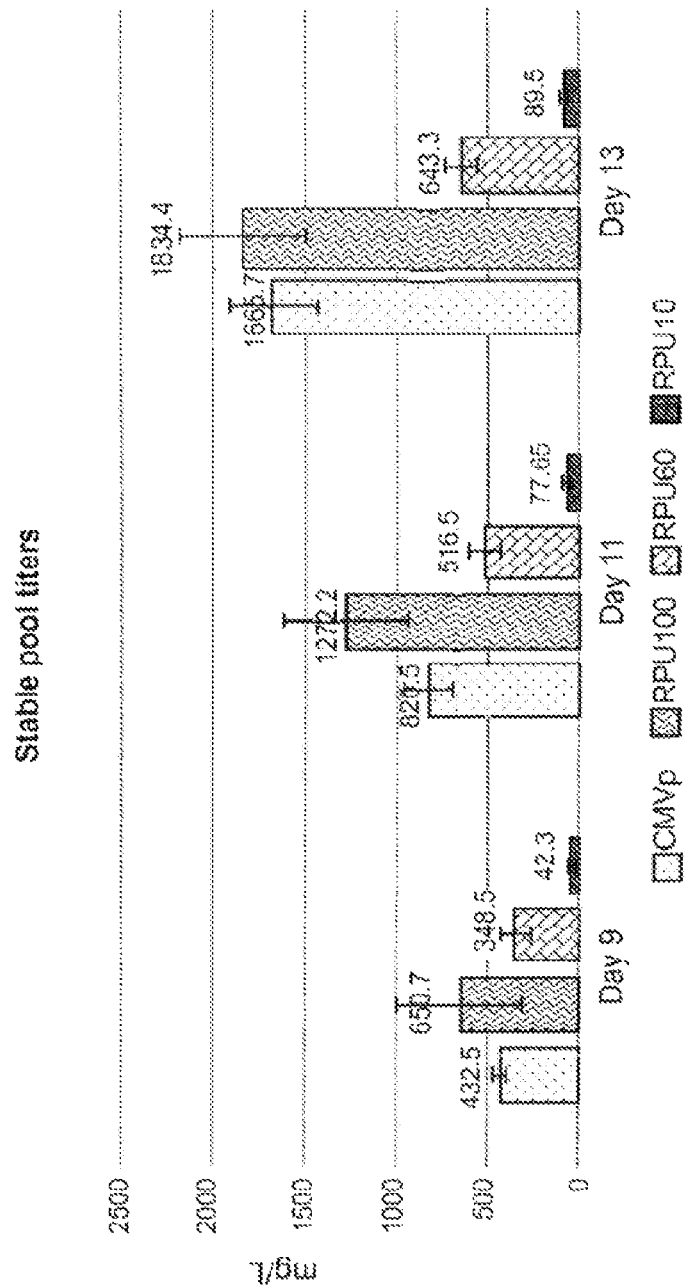

FIG. 8: Stable pool titers. The fed-batch expression levels of an immune activator protein under the control of various promoters is shown in stable CHO pools.

DETAILED DESCRIPTION OF THE INVENTION

I. Definitions

The term "promoter" as used herein defines a regulatory DNA sequence that mediates the initiation of transcription by directing RNA polymerase to bind to DNA and initiating RNA synthesis. Promoters are generally located upstream of a gene. A promoter can comprise, for example, a core promoter and transcription factor regulatory elements.

A "synthetic promoter" refers to an artificial, engineered, and/or assembled promoter comprising transcription factor regulatory elements.

A "transcription factor regulatory element" (TFRE) is a nucleotide sequence that is a binding site for a transcription factor. Exemplary TFREs are provided in Table 1.

A "transcription factor" (TF) is a protein that binds to a TFRE and affects the rate of transcription (either positively or negatively) of a gene.

A "core promoter" refers to a nucleotide sequence that is the minimal portion of the promoter required to initiate transcription. Core promoter sequences can be derived from prokaryotic or eukaryotic genes, including, e.g., the CMV immediate early gene promoter or SV40. A core promoter can comprise, for example, a TATA box. A core promoter can comprise, for example, an initiator element. A core promoter can comprise, for example, a TATA box and an initiator element.

The term "enhancer" as used herein defines a nucleotide sequence that acts to potentiate the transcription of a gene, independent of the identity of the gene, the position of the sequence in relation to the gene, and the orientation of the sequence.

The terms "functionally linked" and "operably linked" are used interchangeably and refer to a functional relationship between two or more DNA segments (e.g., a gene to be expressed and a sequence(s) controlling the gene's expression). For example, a promoter and/or enhancer sequence, including any combination of cis-acting transcriptional control elements, is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

"Orientation" refers to the order of nucleotides in a given DNA sequence. For example, an orientation of a DNA sequence in opposite direction in relation to another DNA sequence is one in which the 5' to 3' order of the sequence in relation to another sequence is reversed when compared to a point of reference in the DNA from which the sequence was obtained. Such reference points can include the direction of transcription of other specified DNA sequences in the source DNA and/or the origin of replication of replicable vectors containing the sequence.

The term "expression vector" as used herein includes an isolated and purified DNA molecule which upon transfection into an appropriate host cell provides for expression of a recombinant gene product within the host cell. In addition to the DNA sequence coding for the recombinant or gene product the expression vector comprises regulatory DNA sequences that are required for an efficient transcription of the DNA coding sequence into mRNA and optionally for an efficient translation of the mRNAs into proteins in the host cell line.

The terms "host cell" or "host cell line" as used herein include any cells, in particular mammalian cells, which are capable of growing in culture and expressing a desired recombinant product protein.

The term "CpG site" as used herein include regions of DNA where a cytosine nucleotide occurs next to a guanine nucleotide in the linear sequence of bases along its length. "CpG" is shorthand for "—C-phosphate-G-", that is, cytosine and guanine separated by only one phosphate; phosphate links any two nucleosides together in DNA. The "CpG" notation is used to distinguish this linear sequence from the CG base-pairing of cytosine and guanine.

The term "expression cassette" as used herein includes a polynucleotide sequence encoding a polypeptide to be expressed and sequences controlling its expression such as a promoter and optionally an enhancer sequence, including any combination of cis-acting transcriptional control elements. The sequences controlling the expression of the gene, i.e. its transcription and the translation of the transcription product, are commonly referred to as regulatory unit. Most parts of the regulatory unit are located upstream of coding sequence of the gene and are operably linked thereto. The expression cassette may also contain a downstream 3'-untranslated region comprising a polyadenylation site. The regulatory unit of the invention is either operably linked to the gene to be expressed, i.e. transcription unit, or is separated therefrom by intervening DNA such as for example by the 5'-untranslated region of the heterologous gene. Preferably the expression cassette is flanked by one or more suitable restriction sites in order to enable the insertion of the expression cassette into a vector and/or its excision from a vector. Thus, the expression cassette according to the present invention can be used for the construction of an expression vector, in particular a mammalian expression vector. The expression cassette of the present invention may comprise one or more e.g. two, three or even more non-translated genomic DNA sequences downstream of a promoter.

The terms "polynucleotide" and "nucleotide sequence" include naturally occurring nucleic acid molecules or recombinantly expressed nucleic acid molecules, which can be isolated from a cell, as well as synthetic molecules, which can be prepared, for example, by methods of chemical synthesis or by enzymatic methods such as polymerase chain reaction (PCR).

The term "polynucleotide sequence encoding a polypeptide" as used herein includes DNA coding for a gene, preferably a heterologous gene expressing the polypeptide.

The terms "heterologous coding sequence", "heterologous gene sequence", "heterologous gene", "recombinant gene" or "gene" are used interchangeably. These terms refer to a DNA sequence that codes for a recombinant, in particular a recombinant heterologous protein product that is sought to be expressed in a host cell, preferably in a mammalian cell and harvested. The product of the gene can be a polypeptide. The heterologous gene sequence is naturally not present in the host cell and is derived from an organism of the same or a different species and may be genetically modified.

The terms "protein" and "polypeptide" are used interchangeably to include a series of amino acid residues connected to the other by peptide bonds between the alpha-amino and carboxy groups of adjacent residues.

II. Methods of Making Synthetic Promoters

Using the methods provided herein, promoters can be designed to have specific functionality, e.g., a desired expression level, expression in desired phases of cell growth, and/or expression in desired cell types. A method for designing a promoter can comprise (i) profiling transcription factor (TF) expression to select TFs, (ii) identifying transcription factor regulatory elements (TFREs) that interact with the selected TFs and that are transcriptionally active in a homotypic promoter, and (iii) determining the relative transcriptional activity of TF-TFRE interactions within a heterotypic promoter. Optionally, a method can further comprise (iv) selecting TFREs with a desired transcriptional activity and (v) producing a synthetic promoter comprising the selected TFREs.

Profiling TF expression can be accomplished experimentally (e.g., by culturing cells and measuring TF RNA and/or protein levels (e.g., as exemplified in Example 1 herein)) or can be accomplished by reviewing data of TF expression patterns. Such profiling can include determining the amount or abundance of TFs (RNA or protein) in an individual cell type, growth phase, or culture condition and/or the variability of the amount or abundance of TFs (RNA or protein) across multiple cell types, growth phases, or culture conditions. Accordingly, a method provided herein can comprise profiling TF expression by comparing expression in at least two cell types, at least two growth phases (e.g., a stationary phase and an exponential growth phase), and/or at least two culture conditions. A method provided herein can comprise profiling TF expression by comparing expression in at least three cell types, at least three growth phases, and/or at least three culture conditions. A method provided herein can comprise profiling TF expression by comparing expression in at least two cell types in at least two growth phases or at least two cell types in at least two culture conditions. A method provided herein can comprise profiling TF expression by comparing expression in at least three cell types in at least two growth phases or at least three cell types in at least two culture conditions. A method provided herein can comprise profiling TF expression by comparing expression (e.g., RNA or protein expression levels, e.g., as exemplified in Example 1 herein) in at least two cell types in at least three growth phases or at least two cell types in at least three culture conditions.

As demonstrated herein, the TF expression can be profiled in a mammalian cell type or in multiple mammalian cell types. The TF expression can be profiled in a CHO cell or in multiple CHO cell types (e.g., CHO-S, CHO-K1, CHO-DG44 and/or CHO-DXB11 cells). The TF expression can be profiled in a cell line expressing a recombinant protein and its parent cell line (i.e., the cell line not expressing the recombinant protein). The TF expression can be profiled in two or more different cell types from the same organism.

Based on expression profiles, TFs can be selected to accomplish a desired goal. For example, TFs that are highly expressed in a particular cell type, growth phase, and/or culture condition can be selected. TFs that are highly expressed across multiple cell types, growth phases, and/or culture conditions can be selected. TFs that are expressed at an intermediate level in a particular cell type, growth phase, and/or culture condition can also be selected.

According to some methods provided herein, TFs that are stably expressed across multiple conditions (e.g. in multiple cell lines and/or multiple growth conditions) are selected. Stability of expression can be determined by measuring the maximum fold change (MFC) in the expression level (protein or RNA (e.g. as exemplified in Example 1 herein)) across the multiple conditions. The MFC is the ratio between the highest and lowest expression levels across the multiple conditions. In certain aspects, the MFC of a stably expressed transcription factor is no more than 3, no more than 2.5, no more than 2, no more than 1.5, no more than 1, or no more than 0.5.

Alternatively, TFs that are only highly expressed in a particular desired cell type, growth phase, and/or a culture condition can be selected. Thus, in some methods TFs that are preferentially upregulated in an intended host cell and/or preferentially down-regulated in an off-target host cell are selected. In some methods, TFs that are preferentially upregulated in an intended cell-cycle phase and/or down-regulated in an off-target cell-cycle phase are selected.

According to the methods provided herein, the expression of at least 25, at least 50, at least 150, at least 200, at least 250, at least 500, or at least 1000 TFs can be profiled.

Cognate binding sites for the selected TFs (i.e., transcription factor regulatory elements (TFREs) that interact with the selected TFs) can be determined, e.g., by review of published studies and online databases. The TFREs that interact with the selected TFs can then be screened to select those that are transcriptionally active in a homotypic promoter. A homotypic promoter comprises repeat copies of a specific TFRE in series. For example, a homotypic promoter can comprise 2 to 20 copies of a TFRE. A homotypic promoter can comprise 4 to 10 copies of a TFRE. A homotypic promoter can comprise about 5, about 6, about 7, or about 8 copies of a TFRE. A homotypic promoter can comprise 5, 6, 7, or 8 copies of a TFRE.

The TFRE in a homotypic promoter can be separated by a spacer. The spacer can be, for example, no more than 50 nucleotides, no more than 25, or no more than 12 nucleotides. The spacer can be, for example 4 to 50 nucleotides, 4 to 25 nucleotides, or 4 to 12 nucleotides. The spacer can be about 6 nucleotides. The spacer can be 6 nucleotides. The TFREs in a homotypic promoter can be separated by the same spacer or can be separated by different spacers.

TFREs that are transcriptionally active in a homotypic promoter can be identified by creating constructs that contain a reporter gene operably linked to a core promoter with multiple upstream copies of the TFRE. The expression level (RNA or protein) of the reporter can be assessed, e.g., after transient transfection in a cell of interest (e.g., a CHO cell such as a CHO-S, CHO-K1, CHO-DG44 and/or CHO-DXB11 cell). Expression of the reporter indicates that the TFRE is active in a homotypic promoter.

The activity of TFREs that interact with the selected TFs and are active in homotypic promoters can then be evaluated in the context of heterotypic promoters. Heterotypic promoters can be created by linking a combination of TFREs in series.

A heterotypic promoter can comprise for example, a total of 2 to 20 TFRE, comprising at least 2, at least 3, or at least 4 different TFREs. A heterotypic promoter can comprise for example, a total of 2 to 20 TFRE, comprising 2 to 10, 3 to 9, or 4 to 8 different TFREs.

The TFREs in a heterotypic promoter be separated by a spacer. The spacer can be, for example, no more than 50 nucleotides, no more than 25, or no more than 12 nucleotides. The spacer can be, for example 4 to 50 nucleotides, 4 to 25 nucleotides, or 4 to 12 nucleotides. The spacer can be about 6 nucleotides. The spacer can be 6 nucleotides. The TFREs in a heterotypic promoter can be separated by the same spacer or can be separated by different spacers. Heterotypic promoters can be created, for example, by mixing combinations of TFRE blocks, e.g., in varying amounts or concentrations.

The relative transcriptional activity of TFREs in heterotypic promoters (i.e., the contribution to overall promoter activity provided by a single copy of each TFRE) can be determined, for example, by modeling the heterotypic promoter activity as a function of TFRE copy number.

A promoter can then be designed, for example, by selecting a combination of TFREs that provide a desired activity such as a particular expression level (e.g., across various cell types, growth phase, and/or culture conditions or only in a particular cell type, growth phase, and/or culture condition).

Synthetic promoters containing the selected combination of TFREs can then be produced, e.g., by chemical synthesis, using recombinant nucleotide technology, or using enzymatic methods such as polymerase chain reaction (PCR).

III. Synthetic Promoters

As provided herein promoters can be designed to have specific functionality, e.g., a desired expression level, expression in desired phases of cell growth, and/or expression in desired cell types.

A promoter provided herein can comprise a nucleotide sequence comprising transcription factor regulatory elements (TFREs) and a promoter core. The nucleotide sequence comprising the TFREs can be upstream of the promoter core.

A promoter provided herein can comprise multiple TFREs, for example 2 to 20, 2 to 18, 2 to 16, 2 to 15, 2 to 14, 3 to 20, 3 to 18, 3 to 16, 3 to 15, 3 to 14, 4 to 20, 4 to 18, 4 to 16, 4 to 15, 4 to 14, 5 to 20, 5 to 18, 5 to 16, 5 to 15, 5 to 14, 6 to 20, 6 to 18, 6 to 16, 6 to 15, or 6 to 14 TFREs.

A TFRE can comprise, consist essentially of, or consist of 4 to 100 nucleotides, 4 to 75 nucleotides, 4 to 50 nucleotides, 4 to 30 nucleotides, 4 to 25 nucleotides, 4 to 20 nucleotides, 4 to 15 nucleotides, or 4 to 12 nucleotides. A TFRE can comprise, consist essentially of, or consist of 6 to 100 nucleotides, 6 to 75 nucleotides, 6 to 50 nucleotides, 6 to 30 nucleotides, 6 to 25 nucleotides, 6 to 20 nucleotides, 6 to 15 nucleotides, or 6 to 12 nucleotides. A TFRE can comprise, consist essentially of, or consist of 8 to 100 nucleotides, 8 to 75 nucleotides, 8 to 50 nucleotides, 8 to 30 nucleotides, 8 to 25 nucleotides, 8 to 20 nucleotides, 8 to 15 nucleotides, or 8 to 12 nucleotides. A TFRE can comprise, consist essentially of, or consist of 4 to 30 nucleotides.

A TFRE can be a mammalian TFRE. A TFRE can be a CHO cell TFRE. A TFRE can comprise the nucleotide sequence of any one of SEQ ID NOs:1-32. A TFRE can be selected from the group consisting of antioxidant RE (ARE) (optionally comprising the nucleotide sequence of SEQ ID NO:7), ETS binding site 1 (EBS1) (optionally comprising the nucleotide sequence of SEQ ID NO:10), endoplasmic reticulum stress RE (ERSE) (optionally comprising the nucleotide sequence of SEQ ID NO:15), and dioxin RE (DRE) (optionally comprising the nucleotide sequence of SEQ ID NO:31) TRFEs. A TFRE can be selected from the group consisting of antioxidant RE (ARE), ETS binding site 1 (EBS1), and dioxin RE (DRE). Optionally, a promoter provided herein can additionally comprise a nuclear factor RE (NF1-RE) (optionally comprising the nucleotide sequence of SEQ ID NO:6), a GC-box (optionally comprising the nucleotide sequence of SEQ ID NO:9), and/or a CCAAT-enhancer binding RE (C/EBP-RE) (optionally comprising the nucleotide sequence of SEQ ID NO:23) TFRE.

Certain promoters provided herein do not comprise an endoplasmic reticulum stress RE (ERSE) TFRE.

Certain promoters provided herein do not comprise a nuclear factor 1 RE (NF1-RE) TFRE. Certain promoters provided herein do not comprise a GC-box TFRE. Certain promoters provided herein do not comprise a CCAAT-enhancer binding protein RE (C/EBP-RE) TFRE. Certain promoters provided herein do not comprise a NF1-RE, GC-box, or C/EBP-RE TFRE.

As provided herein, a promoter can comprise a nucleotide sequence comprising TFREs wherein at least two of the TFREs are the same, e.g., wherein at least two of the TFREs are ARE TFREs, wherein at least two of the TFREs are EBS1 TFREs, at least two of the TFREs are ERSE TFREs, and/or at least two of the TFREs are DRE TFREs. As provided herein, a promoter can comprise a nucleotide sequence comprising TFREs wherein at least three of the TFREs are the same, e.g., wherein at least three of the TFREs are ARE TFREs, wherein at least three of the TFREs are EBS1 TFREs, at least three of the TFREs are ERSE TFREs, and/or at least three of the TFREs are DRE TFREs.

A promoter provided herein can also comprises spacers, e.g., between the TFREs. The spacer can be, for example, no more than 50 nucleotides, no more than 25, or no more than 12 nucleotides. The spacer can be, for example 4 to 50 nucleotides, 4 to 25 nucleotides, or 4 to 12 nucleotides. The spacer can be about 6 nucleotides. The spacer can be 6 nucleotides.

A promoter provided herein can comprise multiple copies of the same spacer (i.e., a spacer of a specified sequence and length) or can comprise a combination of different spacers (i.e., spacers of different sequences and/or varying lengths). Thus, a promoter can comprise the same spacer between each TFRE or can contain different spacers between TFREs.

A nucleotide sequence comprising TRFEs (and optionally spacers) can be up to 1500 nucleotides, up to 1000 nucleotides, up to 750 nucleotides, up to 500 nucleotides, or up to 250 nucleotides. A nucleotide sequence comprising TRFEs (and optionally spacers) can be at least 20 nucleotides.

A nucleotide sequence comprising TRFEs (and optionally spacers) can comprise TFREs, wherein no TFRE is more than 25 nucleotides and wherein no spacer is more than 50 nucleotides. A nucleotide sequence comprising TRFEs (and optionally spacers) can comprise TFREs, wherein no TFRE is more than 25 nucleotides and wherein no spacer is more than 25 nucleotides. A nucleotide sequence comprising TRFEs (and optionally spacers) can comprise TFREs, wherein no TFRE is more than 25 nucleotides and wherein no spacer is more than 20 nucleotides. A nucleotide sequence comprising TRFEs (and optionally spacers) can comprise TFREs, wherein no TFRE is more than 25 nucleotides and wherein no spacer is more than 15 nucleotides. A nucleotide sequence comprising TRFEs (and optionally spacers) can comprise TFREs, wherein no TFRE is more than 25 nucleotides and wherein no spacer is more than 10 nucleotides. As provided herein, such a nucleotide sequence can comprise at least 4 TRFEs.

A nucleotide sequence comprising TRFEs (and optionally spacers) can comprise TFREs, wherein each TFRE is 6 to 20 nucleotides and wherein each spacer is more than 50 nucleotides. A nucleotide sequence comprising TRFEs (and optionally spacers) can comprise TFREs, wherein each TFRE is 6 to 20 nucleotides and wherein each spacer is more than 25 nucleotides. A nucleotide sequence comprising TRFEs (and optionally spacers) can comprise TFREs, wherein each TFRE is 6 to 20 nucleotides and wherein each spacer is more than 20 nucleotides. A nucleotide sequence comprising TRFEs (and optionally spacers) can comprise TFREs, wherein each TFRE is 6 to 20 nucleotides and wherein each spacer is more than 15 nucleotides. A nucleotide sequence comprising TRFEs (and optionally spacers) can comprise TFREs, wherein each TFRE is 6 to 20 nucleotides and wherein each spacer is more than 10 nucleotides. As provided herein, such a nucleotide sequence can comprise at least 4 TRFEs.

A core promoter, as provided herein, can comprise a TATA box and/or an initiator element, optionally wherein the core promoter is 25-100 nucleotides. A core promoter, as provided herein, can be a nucleotide sequence that surrounds the transcriptional start cite of an endogenous gene that is highly expressed in a cell, e.g., a CHO cell. A core promoter, as provided herein, can be a CMV core promoter. Accordingly, a core promoter can comprise, consist essentially of, or consist of the nucleotide sequence of SEQ ID NO:33.

A promoter provided herein can be designed to limit the number of CpG dinucleotides. The methylation of cytosines in CpG dinucleotides can produce instability. Accordingly, a nucleotide sequence comprising TFREs can have less than 20, less than 15, less than 10, less than 9, less than 8, less than 7, or less than 6 CpG dinucleotides. A nucleotide sequence comprising TFREs can have no more than 20, no more than 15, no more than 10, no more than 9, no more than 8, no more than 7, no more than 6, or no more than 5 CpG dinucleotides. Similarly, a promoter provided herein can have less than 20, less than 15, less than 10, less than 9, less than 8, less than 7, or less than 6 CpG dinucleotides. A promoter provided herein can have no more than 20, no more than 15, no more than 10, no more than 9, no more than 8, no more than 7, no more than 6, or no more than 5 CpG dinucleotides.

A promoter provided herein can be designed to limit the number of repeat sequences. Accordingly, a nucleotide sequence comprising TFREs can have no repeat sequences of more than 20 nucleotides, more than 25 nucleotides, more than 30 nucleotides, more than 35 nucleotides, or more than 40 nucleotides. Similarly, a promoter provided herein can have no repeat sequences of more than 20 nucleotides, more than 25 nucleotides, more than 30 nucleotides, more than 35 nucleotides, or more than 40 nucleotides. A nucleotide sequence comprising TFREs can have no more than one repeat sequence, e.g., a repeat sequence of more than 20 nucleotides, more than 25 nucleotides, more than 30 nucleotides, more than 35 nucleotides, or more than 40 nucleotides. A promoter provided herein can have no more than one repeat sequence, e.g., a repeat sequence of more than 20 nucleotides, more than 25 nucleotides, more than 30 nucleotides, more than 35 nucleotides, or more than 40 nucleotides.

A promoter provided herein can be designed to limit the number of restriction endonuclease sites. For example, a nucleotide sequence comprising TFREs or a promoter provided herein can lack EcoRI, BamHI, HindIII, TaqI, NotI, SmaI, PvuI, PacI, KpnI, and/or XhoI restriction endonuclease sites. For example, a nucleotide sequence comprising TFREs or a promoter provided herein can lack EcoRI, BamHI, HindIII, TaqI, NotI, SmaI, PvuI, and/or PacI restriction endonuclease sites. In some embodiments, a nucleotide sequence comprising TFREs or a promoter provided herein can comprise restriction sites (e.g., KpnI or XhoI restriction sites) between TFREs and/or between spacers.

As demonstrated herein, promoters can be designed in which the order, spacing, and orientation of the TFREs have minimal effect on promoter activity. Accordingly, the activity of a promoter can correlate with the number of copies of each TFRE contained within the promoter. The activity of a promoter can therefore be predicted based on the number of copies of each TFRE contained within the promoter.

As demonstrated herein, promoters can also be designed to avoid a significant effect on cell growth, and/or cell viability. A promoter provided herein can avoid promoter silencing and/or minimize off-target effects on key cellular processes that underpin protein production.

IV. Vectors, Cells, and Libraries

Also provided herein are vectors, cells, and libraries comprising the promoters provided herein.

A vector can comprise, for example, a promoter provided herein operably linked to a gene to be expressed or a transcribable polynucleotide. The gene to be expressed can be, for example, a reporter gene such as secreted alkaline phosphatase (SEAP), β-galactosidase (GAL), luciferase (LUC), or green fluorescent protein (GFP). The gene to be expressed can also be a therapeutic protein such as an antibody (or a heavy chain or light chain thereof, or a heavy chain variable region or light chain variable region thereof), an antigen-binding fragment of an antibody (e.g., an ScFv), or an Fc fusion protein. The gene to be expressed can also be an enzyme. The transcribable polynucleotide can be, for example, an RNAi or an shRNA.

A cell can comprise a promoter provided herein or a vector provided herein. The cell can be a mammalian cell, such as a Chinese Hamster Ovary (CHO) cell. The CHO cell can be, for example, a CHO-S, CHO-K1, CHO-DG44, or a CHO-DXB11 cell. The cell can be, for example, a human cell. The cell can also be, for example, a non-human cell, e.g., a non-human mammalian cell. A cell comprising a promoter or vector provided herein can be transiently transfected or stably transfected.

A cell provided herein can be an isolated cell (i.e. a cell not contained within an organism) or a cultured cell (i.e. a cell in culture).

A library can comprise promoters provided herein, vectors provided herein, or cells provided herein. The library can comprise at least 50, at least 100, at least 150, at least 200, at least 250, or at least 500 different promoters, vectors, or cells.

V. Working Examples

Example 1: Materials and Methods

Analysis of Host Cell Transcription Factor Expression Dynamics

Total RNA was extracted from three CHO-K1-derived cell lines (parental host cell line, and host expressing either glutamine synthetase (GS) or GS and an IgG antibody) during exponential and stationary phases of growth using RNAeasy mini kits (Qiagen, Crawley, UK). RNA purity and integrity were confirmed using a NanoDrop spectrophotometer (Thermo Fisher Scientific, Paisley, UK) and 2100 Bioanalyzer (Agilent Technologies, Wokingham, UK). RNA-seq libraries were prepared using the TruSeq RNA library preparation kit (Illumina, Essex, UK) and sequenced using an Illumina HiSeq 2000 system (Illumina). Sequence reads were mapped to the CHO-K1 reference genome using Tophat (24,25), and the relative abundance of each transcript was calculated using Cufflinks (26). A curated database of experimentally validated mouse transcription factors (TFs) was obtained from TFcheckpoint (27,28). The mean transcript abundance of each TF gene across all six experimental conditions was determined, and genes with expression levels above the $70^{th}$ percentile were selected for further analysis. Gene expression stability was measured by calculating the maximum fold change (MFC) in transcript abundance across all transcriptomes. Cognate binding sites of stably expressed TFs (MFC <1.5) were obtained from previously published studies and online databases ((29); see Table 1).

TABLE 1

Transcription factor regulatory element consensus sequences.

| Transcription Factor Response/ Regulatory Element (RE) | Sequence (SEQ ID NO.) |
|---|---|
| Enhancer box (E-box) | CACGTG (SEQ ID NO: 1) |
| cAMP RE (CRE) | TGACGTCA (SEQ ID NO: 2) |
| Amino acid RE (AARE) | ATTGCATCA (SEQ ID NO: 3) |
| Forkhead box binding site (FBS) | ATAAACAA (SEQ ID NO: 4) |
| Nuclear factor kappa B (NFkB-RE) | GGGACTTTCC (SEQ ID NO: 5) |
| Nuclear factor 1 RE (NF1-RE) | TTGGCTATATGCCAA (SEQ ID NO: 6) |
| Antioxidant RE (ARE) | ATGACACAGCAAT (SEQ ID NO: 7) |
| Elongation factor 2 RE (E2F-RE) | TTTCGCGC (SEQ ID NO: 8) |
| GC-box | GGGGCGGGG (SEQ ID NO: 9) |
| ETS binding site 1 (EBS1) | ACCGGAAGT (SEQ ID NO: 10) |
| ETS binding site 2 (EBS2) | ACAGGAAGT (SEQ ID NO: 11) |
| Unfolded protein response element (UPRE) | GCTGACGTGGTGCTGACGTGG (SEQ ID NO: 12) |
| Endoplasmic reticulum stress RE II (ERSE-II) | ATTGGTCCACG (SEQ ID NO: 13) |
| Yin Yang 1 RE (YY1-RE) | CGCCATTTT (SEQ ID NO: 14) |
| Endoplasmic reticulum stress RE (ERSE) | CCAATGGCCAGCCTCCACG (SEQ ID NO: 15) |
| Sterol RE (SRE) | ATCACCCCAC (SEQ ID NO: 16) |
| Peroxisome proliferator RE (PPRE) | AGGTCAAAGGTCA (SEQ ID NO: 17) |
| Signal transducer and activator of transcription RE (STAT-RE) | TTCCAGGAA (SEQ ID NO: 18) |
| CACCC-box | CCACACCC (SEQ ID NO: 19) |
| SMAD binding element (SBE) | GTCTGCAGAC (SEQ ID NO: 20) |
| Thyroid response element 1 (TRE1) | AGGTCACTTCAGGTCA (SEQ ID NO: 21) |
| Thyroid response element 2 (TRE2) | TGACCTTGGCATAGGTCA (SEQ ID NO: 22) |
| CCAAT-enhancer binding protein RE (C/EBP-RE) | TTGCGCAA (SEQ ID NO: 23) |
| MCAT | ACATTCCTG (SEQ ID NO: 24) |
| Cellular myeloblastosis RE (cMyb-RE) | TAACGG (SEQ ID NO: 25) |
| Heat shock element (HSE) | AGAACATTCTAGAA (SEQ ID NO: 26) |
| Estrogen-related receptor RE (ERRE) | AGGTCATTTTGACCT (SEQ ID NO: 27) |
| Metal RE (MRE) | TGCACACAGCC (SEQ ID NO: 28) |
| D-box | ATTATGTAAC (SEQ ID NO: 29) |
| Hypoxia RE (HRE) | GTACGTGC (SEQ ID NO: 30) |
| Dioxin RE (DRE) | GCTTGCGTGAGAAG (SEQ ID NO: 31) |
| CC(A/T)$_6$GG element CArG | CCAAATTTGG (SEQ ID NO: 32) |

In Vitro-Construction of Homotypic and Heterotypic Promoters

A minimal CMV core promoter (Genbank accession number M60321.1, nucleotides 1109-1193: AGGTC-TATATAAGCAGAGCTCGTTTAGTGAACCGTCA-GATCGCCTAGATACG CCATC-CACGCTGTTTTGACCTCCATAGAAGAC (SEQ ID NO:33)) was synthesized (Sigma, Poole, UK) and inserted upstream of the secreted alkaline phosphatase (SEAP) gene in a previously described promoterless reporter vector (30). To construct homotypic TFRE-reporters, synthetic oligonucleotides containing six repeat copies of a specific TFRE in series (see Table 1) were inserted upstream of the CMV core promoter. To create libraries of heterotypic promoters, TFRE building blocks containing a single copy of a discrete TF binding sequence were constructed as previously described (31), and ligated together in varying combinations with T4 DNA ligase (Thermo Fisher Scientific). A 'cloning-block' containing KpnI and XhoI restriction endonuclease sites was included in ligation mixes at a 1:20 molar ratio to TFRE blocks. Random TFRE block-assemblies were digested with KpnI and XhoI (Promega, Southampton, UK), gel extracted (Qiaquick gel extraction kit, Qiagen), and inserted upstream of the CMV core promoter in SEAP-reporter vectors. Plasmids were sequenced to determine the TFRE-composition of each in vitro-constructed synthetic promoter.

Modeling of Heterotypic Promoter Activities

In vitro-constructed heterotypic promoter activities were modeled as a function of constituent TF binding site copy numbers. A comparison of different modeling approaches (linear regression, generalized linear, generalized additive, Gaussian process) determined that all models had equivalent predictive power. Accordingly, to minimize complexity, we used a multiple linear regression model $\hat{Y}=\beta_0+\beta_1 x_1+\beta_2 x_2+\ldots\beta_{12}x_{12}$ where $\hat{Y}$ represents promoter activity, and $x_1$-$x_{12}$ are the copy numbers of 12 discrete TFRE blocks. Regression coefficients ($\beta_1$-$\beta_{12}$; calculated using least-squares estimation, $\hat{\beta}=(X^TX)^{-1}X^Ty$) were analyzed to determine the relative transcriptional activity of a single copy of each TFRE block within heterotypic promoter architectures. The predictive ability of the model, and the possibility of overfitting, were assessed using leave-one-out and five-fold cross-validations.

In Silico Design of Heterotypic Promoters

Every possible 1-14 block combination of twelve discrete TF binding sites (n=9,657,699) was generated using the 'combinations' function in R. The relative transcriptional activity of each TFRE-combination was determined using our model of in vitro-constructed heterotypic promoter activities. TFRE-combinations with desired design criteria were selected from the library by applying successive filtration steps (as described in Examples 2-5). Constituent TFREs were arranged to minimize the occurrence of CpG dinucleotides, repeat sequences, and restriction endonuclease sites. To aid this process, binding sites were separated with specifically designed 6 base pair (bp) spacer sequences. Designed promoter sequences were analysed for the presence of repeat sequences and endonuclease sites using FAIR (http://bioserver1.physics.iisc.ernet.in/fair/) and Webcutter (http://rna.lundberg.gu.se/cutter2/) (32). To confirm that unintended, additional TF binding sites had not been created at TFRE-spacer junctions, promoters were analyzed using MatInspector (https://www.genomatix.de/matinspector.html) and Transcription Affinity Prediction tool (TRAP: http://trap.molgen.mpg.de/cgi-bin/trap_form.cgi) (33,34). Designed sequences were synthesized (GeneArt, Regensburg, Germany) and cloned upstream of the minimal CMV core promoter in SEAP-reporter vectors.

CHO Cell Culture and Transfection

Chinese hamster ovary (CHO) cells (CHO-K1-derived) were routinely cultured in CD-CHO medium (Thermo Fisher Scientific) at 37° C. in 5% (v/v) $CO_2$ in vented Erlenmeyer flasks (Corning, UK), shaking at 140 rpm, and subcultured every 3-4 days at a seeding density of $2\times10^5$ cells/ml. Cell concentration and viability were determined by an automated Trypan Blue exclusion assay using a Vi-Cell cell viability analyser (Beckman-Coulter, High Wycombe, UK). Two hours prior to transient transfections, $2\times10^5$ cells from a mid-exponential phase culture were seeded into individual wells of a 24-well plate (Nunc, Stafford, UK). Cells were transfected with DNA-lipid complexes comprising DNA and Lipofectamine (Thermo Fisher Scientific), prepared according to the manufacturer's instructions. Internal controls (hCMV-IE1-SEAP, SV40-SEAP, NFkB-RE-SEAP) were included in each plate to confirm reproducible transfection performance and normalize synthetic promoter activities. Transfected cells were incubated for 24 hours prior to quantification of SEAP protein expression using the Sensolyte pNPP SEAP colorimetric reporter gene assay kit (Cambridge Biosciences, Cambridge, UK). To confirm that SEAP activities in cell culture supernatants were correlated with SEAP mRNA levels, total RNA was extracted from selected transfected cells and analysed by quantitative PCR (qPCR).

To construct stable pools, synthetic promoter-SEAP reporter plasmids (5 µg) coexpressing a glutamine synthetase selection marker gene were transfected into CHO cells ($1\times10^7$; triplicate transfections) by electroporation using the Amaxa Nucleofector system (Lonza, Slough, UK). Stable transfectants were selected in 50 µM methionine sulfoximine (Sigma). For batch-production processes, $6\times10^6$ cells from a mid-exponential phase culture were inoculated into 30 mL CD-CHO medium in vented Erlenmeyer flasks. Cell concentration, culture viability and SEAP expression (at mRNA and protein levels) were measured during exponential (day 4) and stationary (day 7) growth phases. To validate long-term expression stability, 7-day batch-production processes were repeated after high and low producer stable pools had been subcultured in MSX-containing medium for 8 weeks (60 cell generations).

RNA Extraction, Reverse Transcription, and qPCR Analysis

Total RNA was extracted from cells using RNeasy mini kits (Qiagen, UK). RNA purity and integrity were confirmed using a NanoDrop spectrophotometer (Thermo Fisher Scientific) and 2100 Bioanalyzer (Agilent Technologies). 800 ng of extracted RNA was reverse transcribed using the Quantitect reverse transcription kit (Qiagen), according to manufacturer's instructions (genomic DNA was eliminated during this procedure). cDNA was diluted 1:10 in nuclease-free water prior to qPCR analysis using a 7500 fast real-time PCR system (Applied Biosystems, Cheshire, UK). Reaction mixtures containing 12.5 µl QuantiFast SYBR green PCR master mix (Qiagen), 2 µl cDNA, 2.5 µl primer mix (final concentration of 200 nM per primer), and 8 µl nuclease free water were prepared in MicroAmp fast optical 96-well plates (Applied Biosystems). Amplification conditions were as follows: 95° C. for 5 min, followed by 40 cycles at 95° C. for 15 s and 60° C. for 60 s. Melting curve analysis was performed from 60-95° C. Gnb1 and Fkbp1a were used as internal control reference genes (Brown A J et al. *Transcriptome-based identification of the optimal reference CHO genes for normalisation of qPCR data. Biotechnology Journal* 13: 1700259 (2017)). Reaction mixtures containing no template, or products from reverse transcription reactions performed in the absence of reverse transcriptase, were used as negative controls. All samples were run in triplicate and mean Ct (cycle threshold) values were used for further analysis. Primer sequences are listed in Table 2. Amplification efficiencies were determined from standard curves (10-fold serial dilutions of pooled cDNA samples) using the equation E=10 (−1/slope).

TABLE 2 qPCR primer sequences and amplification efficiencies.

| Gene | Primer sequences | Primer Efficiency |
| --- | --- | --- |
| Gnb1 | CCATATGTTTCTTTCCCAATGGC AAGTCGTCGTACCCAGCAAG (SEQ ID NO: 34) | 98.39% |
| Fkbp1a | CTCTCGGGACAGAAACAAGC GACCTACACTCATCTGGGCTAC (SEQ ID NO: 35) | 99.09% |
| Seap | GAATCGGGCCAAGAAAGCAG ATGAGCTGCGTAGCGATGTC (SEQ ID NO: 36) | 98.70% |

Example 2: Analysis of Host-Cell TF Expression Dynamics Facilitates Identification of Modular Binding Sites with Context-Specific Functionalities To demonstrate a process of custom promoter design, sequences were created for use in CHO cells, the predominant host for the production of biopharmaceuticals. Whilst transcriptional control has previously been demonstrated in CHO cells, in vitro construction methods have not enabled customizable specification of sequence features in order to prevent promoter silencing and minimize off-target effects on key cellular processes that underpin protein production (31,35,36). To profile the TF repertoire of CHO cells, TF expression levels were analyzed in three discrete CHO cell lines (CHO-K1 derived parental host cell line, and host expressing either GS, or GS and an IgG antibody), sampled at exponential and stationary phases of culture. Given the difficulty of directly measuring effective TF concentrations (i.e. TFs that are appropriately modified and localized in the nucleus), TF expression was determined at the mRNA level. Whilst this does not allow precise quantification of active TF levels, it does provide information on general TF expression patterns (e.g. no/low/high/differential expression), enabling identification of cognate TFREs with corresponding activity dynamics (22,23,37). Moreover, this method is easily applicable to promoter design for most mammalian cell types, for which transcriptomic datasets are typically available (38).

Whilst it is estimated that mammalian genomes contain ~2,000 TF-encoding genes, only a fraction of these have been experimentally-verified as DNA-binding TFs (39,40). Accordingly, analysis was restricted to the 774 TFs that have been shown to both exhibit sequence-specific DNA binding and regulate RNA polymeraseII-dependent transcription (27). The mean expression level of each TF across all six experimental conditions was determined. As shown in FIG. 1, 388/774 TFs are expressed in CHO cells, where expression levels span over three orders of magnitude. Depending on required functionalities, synthetic promoters can be designed to interact with any combination of available host-cell TF-parts. For example, cell type-specificity could be achieved by designing promoters to bind TFs that are preferentially upregulated in the intended host cell, and specifically downregulated in cell types where off-target activity is undesirable. In this example, promoters were designed to have minimal impact on the CHO cell processes that underpin protein production, such as proliferation and cell survival. Therefore, TFs that are relatively highly expressed in CHO cells (ranked in the top 30% of TF mRNA expression levels) were targeted based on the reasoning that heterologous promoters can interact with these abundant cellular components without affecting the host cell transcriptome (i.e. these TFs are unlikely to become limiting if the nuclear copies of their cognate binding sites are moderately increased) (41). Further, promoters were designed to exhibit stable activities in the context of different CHO cell lines and growth phases by focusing the search on TFs that displayed high expression stability across all six CHO cell transcriptomes, measured as a maximum fold change (ratio between the highest and lowest expression level) of less than 1.5. Finally, to minimize the risk of silencing, promoters were designed not to interact with TFs that primarily function as repressors (42,43). Application of these selection criteria identified 67 CHO cell TFs with requisite expression profiles and functionalities (FIG. 1A).

As shown in FIG. 1B, due to binding site redundancy (overlap), the 67 identified TFs theoretically interact with 32 discrete regulatory elements. TFREs that are transcriptionally active in the context of homotypic promoters are unlikely to function synergistically when combined together in heterotypic architectures (18). Accordingly, to identify modular TFREs that do not cooperatively interact, we created SEAP reporter constructs that each contained six repeat copies of a specific TFRE in series, upstream of a minimal mammalian core promoter (hCMV-IE1 core containing a TATA box and an initiator element; hCMV-IE1 core promoter and TFRE consensus sequences are shown in SEQ ID NO:33 and Table 1, respectively). Measurement of SEAP reporter production after transient transfection of CHO cells with each TFRE-reporter plasmid showed that 12/32 TFREs could independently mediate activation of recombinant gene transcription (E-box, CRE, AARE, NFkB-RE, ARE, GC-box, EBS1, ERSE, C/EBP-RE, D-box, HRE, DRE). As depicted in FIG. 1B, relative TFRE activities were not proportional to cognate TF expression levels. This may be explained by a lack of correlation between mRNA expression levels and effective TF concentrations. Additionally, in order to drive transcription, some TFs may require combinatorial interactions, or co-activators that are not sufficiently expressed in CHO cells.

Example 3: The Function of Modular TFRE-Blocks in Heterotypic Promoter Architectures is Independent of Binding Site Order and Spacing To test the hypothesis that TFREs that are transcriptionally active in homotypic promoters do not function synergistically when combined together in the context of heterotypic architectures, promoters were constructed with varying TFRE-compositions. For each of the 12 TFREs identified as active in homotypic promoters, oligonucleotide building blocks were synthesized containing a single copy of the TF binding sequence. TFRE blocks were ligated to assemble random strings of TF binding sites, which were inserted upstream of the minimal CMV core promoter in SEAP reporter plasmids. As shown in FIG. 2A, seven distinct promoter libraries were constructed by mixing varying combinations of TFRE blocks. Library TFRE-compositions were designed to test the activity of each individual TFRE in varying promoter (e.g. different strengths, varying TFRE-combinations) and binding site (e.g. varying copy number, orientation, and spatial positioning) contexts. Measurement of SEAP production after transfection of CHO cells with 140 discrete synthetic promoter-reporter plasmids is shown in FIG. 2B. These data show that promoter activities spanned two orders of magnitude, where the most active promoter exhibited a 2.3-fold increase in SEAP production over that deriving from a control vector containing the potent human cytomegalovirus immediate early 1 promoter (hCMV-IE1; GenBank accession number M60321.1, nucleotides 517-1193). With the exception of library 5, promoter activities within each library varied by at least an order of magnitude, where the mean activity of each library ranged from 5.2-61.5 relative promoter units (RPU). To check that SEAP activities in cell culture supernatants were linearly correlated with SEAP mRNA levels, mRNA was extracted from transfected cells and analysed by qPCR. This analysis confirmed that the SEAP production from each plasmid was directly proportional to relative promoter activities (FIG. 6).

Given that TFREs were specifically selected for their putative modular function in heterotypic architectures, it was hypothesized that promoter activities would simply be a function of the relative transcriptional activity contributed by each TF binding site, independent of TFRE orientation, spacing, or order (FIG. 3A). To test this assumption, and to determine the activity of each TFRE in heterotypic architectures, promoters were sequenced to reveal their TFRE-compositions, and promoter activities were modeled as a function of TFRE copy numbers (promoter length varied between 4 and 18 TF binding sites (mean=9)). The resulting linear regression model had high predictive power, where observed and predicted values for promoter activity were highly correlated (leave-one-out cross-validation $r^2$=0.90) (FIG. 3B). To assess the possibility of overfitting the model, was analyzed using five-fold cross-validation (FIG. 3B). The correlation between observed and expected promoter activities was similarly high ($r^2$=0.87), validating the predictive ability of the model. These data show that promoter activities were predominantly a function of the type and quantity of constituent TFREs. These constructed sequences therefore function as "billboard promoters", where the relative organization of composite TF binding sites has minimal influence on promoter activity (19,20). Accordingly, the original hypothesis was confirmed, validating our method for identifying modular TFREs that do not interact combinatorially, and paving the way for simple in silico promoter design.

As the only predictor variables in the model are the number of copies of each TF binding site, the model coefficients represent the contribution a single copy of each TFRE makes to overall promoter activities. Analysis of model coefficients identified that within the context of heterotypic promoters only 7/12 TFREs were transcriptionally active (NFkB-RE, ARE, DRE, ERSE, GC-box, C/EBP-RE, EBS1; p=<0.01), where the remaining five were either transcriptionally inactive (AARE, HRE, E-box), or transcriptionally repressive (D-box, CRE; p=<0.01). As shown in FIG. 3C, TFRE transcriptional activities in heterotypic architectures ranged from −35-100 relative TFRE-activity units. Accordingly, activity in the context of homotypic promoters was not predictive of TFRE activity in heterotypic promoters. It is well known that TFREs can exhibit differential function dependent on the quantity of concatenated binding sites (16,18,44,45). Given that TFREs occurred in 6× repeat copies in homotypic promoters, and typically 1× repeat copies in heterotypic promoters, it is not surprising that some were active in the former and inactive/repressive in the latter. Whilst it would therefore be ideal to assess TFRE activities in single site-copy homotypic promoters, the transcriptional output from a single TF binding site is rarely sufficient to drive detectable levels of recombinant gene expression (16,18). Accordingly, for identification of modular TFREs that are transcriptionally active in single-copy repeats, the two-step screening method developed here is recommended, whereby, i) multisite-copy homotypic promoters are created to identify TFREs that do not interact combinatorially, and ii) multi TFRE-synthetic elements are constructed to determine the relative activity of each TFRE in heterotypic promoters.

Example 4: In Silico Design of Promoters with Context-Specific Functionalities

Given that the model of promoter activities had both high predictive power and simple explanatory variables (i.e. TFRE copy numbers), it was hypothesized that it would be possible, for the first time, to demonstrate the in silico design of mammalian promoters that exhibit predictable activities in vitro. To test this, seven promoters containing a single copy of each TFRE that was transcriptionally active in heterotypic architectures (NFkB-RE, ARE, DRE, ERSE, GC-box, C/EBP-RE, EBS1) were designed. To further confirm that TFRE order and spacing have minimal effect on promoter activity, the seven constituent TF binding sites were arranged in completely different orders within each construct (FIG. 4A). According to the model, as these promoters share identical TFRE-compositions, they should exhibit the same level of activity in vitro (37.3 RPU). Synthetic promoters were chemically synthesized and inserted upstream of the minimal CMV core promoter in SEAP reporter vectors. Measurement of SEAP production after transient transfection of CHO cells with each reporter plasmid showed that promoter activities ranged from 30.2-43.3 RPU (coefficient of variation=9.8%) (FIG. 4B). Therefore, the in vitro activity of all designed promoters was within 7 RPU of the predicted activity, corresponding to an error range of ±18%, where there was only a 1.4-fold difference in expression between the strongest and weakest promoter. It has previously been shown that promoters with the same TFRE composition but different TFRE orders can vary in activity by as much as 5-fold when constituent binding sites exhibit combinatorial interactions (18). The data provided herein therefore further support the conclusion that TFREs specifically selected for putative modular function (i.e. transcriptionally active in homotypic architectures) do not interact cooperatively when combined together in heterotypic promoters. Moreover, they confirm the original hypothesis that promoters can be synthetically designed to exhibit predictable activities.

The ability to combine TFREs in customizable combinations and orders enables the design of promoters with context-specific functionalities. To demonstrate this, promoters that are specifically optimized to function in the context of recombinant protein production in CHO cells were designed. The total number of TF binding sites that could occur within a promoter was limited to fourteen, the quantity contained in the strongest in-vitro-constructed heterotypic promoter. Previous studies of transcriptional activity in CHO cells suggest that it is not possible to significantly increase promoter activity above 100 RPU (2.3-fold higher than hCMV-IE1 (31)). Accordingly, it was assumed that an increase in binding site quantity above fourteen would impose an unnecessarily increased burden on cellular machinery, increasing the potential for off-target effects on the CHO cell transcriptome (2,3).

Utilizing the twelve modular TFRE-parts, 9,657,699 TFRE-combinations can be created with total binding site copy numbers ranging from 1-14. Each of these combinations was constructed and tested in silico, using the model of heterotypic promoter activities to determine relative synthetic promoter strengths. Combinations were then selected according to the specific promoter design criteria that are required for biopharmaceutical production in CHO cells. For example, to minimize the risk of promoter silencing, any combination containing a TFRE that was shown to exhibit transcriptional repressor function in heterotypic promoters (CRE, D-box; FIG. 3C) (42,43) was discounted. Further, given that recombinant protein overexpression in CHO cells can induce the unfolded protein response (46), all promoters containing the ER stress-response element (ERSE) were also disregarded in order to prevent formation of an ER-stress-recombinant gene expression positive feedback loop that could inhibit restoration of proteostasis (47,48). Moreover, to reduce the possibility of synthetic elements causing off-target effects on key CHO cell processes, i) promoters containing TFREs that were inactive in heterotypic architectures were discounted (AARE, HRE, E-box; FIG. 3C) and ii) combinations where the copy number of each TFRE was minimized were selected (2,3,15). With respect to the latter, it was assumed that for each TFRE there is a threshold site copy number above which adding further copies will lead to a level of TF sequestration sufficient to cause changes in endogenous gene expression profiles. However, as TFREs were specifically selected according to high expression of their cognate TFs in CHO cells, it was reasoned that this 'maximum quantity' would be relatively high for each binding site. Accordingly, promoters were chosen in order to limit the copy number of the most abundant constituent-TFRE (e.g. a promoter containing one copy of four different TFREs was preferred to a construct containing two copies of two different TFREs). Finally, as the optimal rate of transcription varies for each recombinant gene, dependent on polypeptide-specific folding and assembly rates, multiple discrete TFRE-combinations were selected in order to enable a wide range of different transcriptional outputs (5, 10, 20, 40, 60, 80, and 100 RPU). As an example, a promoter with the TFRE-composition 2×ARE: 1×C/EBP-RE: 1×GC-box: 1×EBS1: 1×DRE: 1×NFkB-RE was selected as it met all requisite design criteria and had a predicted activity of 40.2 RPU.

When TFRE order, spacing, and orientation have minimal effect on promoter activity, constituent TF binding sites can be optimally arranged to minimize the occurrence of undesirable sequence features. Moreover, in silico-construction facilitates the incorporation of spacer sequences that can be utilized to further improve sequence characteristics. Accordingly, constituent TFREs were arranged within each promoter, and separated with specifically-designed 6-bp spacers, in order to maximize recombinant gene expression stability. For example, given that promoter methylation-mediated epigenetic silencing has been shown to cause production instability in CHO cells, the number of CpG dinucleotides within each was minimized (35,49). Further, as gene silencing can also be caused by deletion of DNA segments via homologous recombination (50,51), the occurrence of repeat sequences was specifically prevented. Given that eukaryotic machinery can recombine identical sequences longer than 40 bp, it was reasoned that preventing intra-promoter repeats larger than 20 bp, and avoiding the repetition of any two-string TFRE block (e.g. ARE-DRE), would provide robust protection against homologous recombination-mediated silencing (52). Moreover, to protect against recombination-mediated gene deletion when multiple promoters are used in conjunction (e.g. expression of monoclonal antibodies), inter-promoter repeat sequences larger than 35 bp were specifically precluded (53-55). Utilizing in silico arrangement of TFREs and spacers, the synthetically designed promoters contained an average of 5.2 CpG dinucleotides and 0 intra-promoter repeats >20 bp. Comparison to the in vitro-constructed heterotypic promoters, which contained an average of 20.7 CpG dinucleotides and 3.8 intra-promoter repeats >20 bp, and the hCMV-IE1 promoter (34 CpG dinucleotides, 1 repeat >20 bp) emphasizes the advantages of in silico promoter design. Additionally, to facilitate cloning into diverse expression vectors, promoters were designed to minimize the occurrence of restriction endonuclease sites (263/308 analyzed restriction sites do not occur in any promoter). Finally, to prevent improper regulation of promoter activity, all sequences were checked to ensure that additional, 'accidental TF binding sites' had not been created at TFRE-spacer junctions.

Example 5: Custom-Designed Sequences Exhibit Predictable Functionalities In Vitro For each desired promoter activity level, two synthetic sequences were designed with different TFRE-compositions (Table 3) (FIG. 5A).

TABLE 3

| De novo designed synthetic promoter sequences | |
|---|---|
| Designed activity level (relative promoter units (RPU)) | Sequence |
| 5 RPU construct 1 | TATAGGAAGGTCTTACCGGAAGTTCCTTAGCTGATAGTATACCAGATTT TTTGCGCAATTCTAGACTGATCATCTAACGACCTATTACCGGAAGTTAG TATG (SEQ ID NO: 37) |
| 5 RPU construct 2 | AAGGTCCTGATATGGGGCGGGGACTAGACAGTATGGTTAGAGACCTAT TACCGGISAGTTCCTTAGGTATACTCTAACCAGATTTMGCGCAATTTG ATCA (SEQ ID NO: 38) |
| 10 RPU construct 1 | TGGGGCGGGGAGTATACGACCTATTTTGCGCAATTCTGATAAAGGTCTT ACCGGAAGTTCAGATTTATAGGTTTTGCGCAATTAGTATGCCTTAGTGG GGCGGGGA (SEQ ID NO: 39) |

TABLE 3-continued

De novo designed synthetic promoter sequences

| Designed activity level (relative promoter units (RPU)) | Sequence |
|---|---|
| 10 RPU construct 2 | TTACCGGAAGTTAAGGTCTTTTGCGCAATTCAGATTGACCTATTACCGG AAGTTTATAGGTGGGGCGGGGAGTTAGATTTTGCGCAATTTGATCATTA CCGGAAGTT (SEQ ID NO: 40) |
| 20 RPU construct 1 | TTACCGGAAGTTGACCTATGCTTGCGTGAGAAGAGTTAGATGGGGCGG GGAAAGGTCTTTTGCGCAATTCAGATTTTACCGGAAGTTTATAGGATGA CACAGCAAT (SEQ ID NO: 41) |
| 20 RPU construct 2 | TGGGGCGGGGACAGATTTTACCGGAAGTTTATAGGTTTTGCGCAATTAG TATGTGGGGCGGGGATCTAACATGACACAGCAATAAGGTCTTACCGGAA GTTGACCTATGGGGCG GGGA (SEQ ID NO: 42) |
| 40 RPU construct 1 | TTTTGCGCAATTTATAGGTGGGGCGGGGAAAGGTCATGACACAGCAATC AGATTTGCTTGCGTGAGAAGAAGTATGTTACCGGAAGTTGACCTATGGG ACTTTCCATCTAACATG ACACAGCAAT (SEQ ID NO: 43) |
| 40 RPU construct 2 | TTACCGGAAGTTCCTTAGTGCTTGCGTGAGAAGAGTATACTGGGGCGGG GACTAGACTTACCGGAAGTTTGATCAATGACACAGCAATAGTATGTGCT TGCGTGAGAAGAGACCTATGGGACTTTCCACCTTAGTTACCGGAAGTT (SEQ ID NO: 44) |
| 60 RPU construct 1 | TTACCGGAAGTTCTAGACTGCTTGCGTGAGAAGAGACCTAATGACACAGCA ATTCTAACTGGGGCGGGGAGTATACTGGGACTTTCCATGATCATTACCGGA AGTTCAGATTTTTTGCGCAATTTATAGGTGCTTGCGTGAGAAGAAAGGTCTG GGACTTTCCAAGTATGATGACACAGCAAT (SEQ ID NO: 45) |
| 60 RPU construct 2 | TGGGGCGGGGAGTTAGATGGGACTTTCCACAGATTTTACCGGAAGTTCTGAT ATGGGGCGGGGAGTATACTGCTTGCGTGAGAAGATATAGGTGGGACTTTCCA CCTTAGTGGGGCGGGGACTAGACATGACACAGCAATTCTAACTTACCGGAAG TTTGATCATGGGACTTTCCA (SEQ ID NO: 46) |
| 80 RPU construct 1 | TGGGGCGGGGAAGTATGATGACACAGCAATTGATCATGGGACTTTCCAC TAGACTGCTTGCGTGAGAAGAAAGGTCTTACCGGAAGTTGACCTAATGAC ACAGCAATGTTAGATGCTTGCGTGAGAAGACTGATATGGGACTTTCCAGT ATACTGGGGCGGGGATCTAACTGGGACTTTCCACAGATTATGACACAGCA AT (SEQ ID NO: 47) |
| 80 RPU construct 2 | TGGGACTTTCCAAGTATGTGCTTGCGTGAGAAGAGACCTATGGGGCGGG GATCTAACATGACACAGCAATCAGATTTGGGACTTTCCAAAGGTCTTTTG CGCAATTCTGATATGCTTGCGTGAGAAGAGTATACTGGGACTTTCCACCT TAGTTACCGGAAGTTTATAGGTGGGACTTTCCACTAGACATGACACAGCA AT (SEQ ID NO: 48) |
| 100 RPU construct 1 | TGGGACTTTCCACTAGACATGACACAGCAATCTGATATGCTTGCGTGAGA AGAGGATTCATATCCTGGGACTTTCCACAGATTTTACCGGAAGTTGTTAG ATGCTTGCGTGAGAAGATCTAACATGACACAGCAATCCTTAGTGGGACTT TCCAAGTATGTGGGCGGGGAGTATACATGACACAGCAATTGATCATTAC CGGAAGTTTATAGGTGGGACTTTCCAGACCTATGCTTGCGTGAGAAGAA AGGTCTGGGACTTTCCA (SEQ ID NO: 49) |
| 100 RPU construct 2 | TGGGACTTTCCACCTTAGATGACACAGCAATCAGATTTGCTTGCGTGA GAAGATATAGGATGACACAGCAATCTAGACTGGGACTTTCCACTGATA TTTTGCGCAATTGACCTAATGACACAGCAATAGTATGTGGGGCGGGGAT CTAACTGGGACTTTCCAAAGGTCTTACCGGAAGTTGTTAGAATGACACA GCAATGGATTCATATCCTGGGACTTTCCAGTATACTGCTTGCGTGAGAAG ATGATCATGGGACTTTCCA (SEQ ID NO: 50) |

Synthetic promoters were chemically synthesized and inserted upstream of the minimal CMV core promoter in SEAP reporter vectors. Measurement of SEAP production after transient transfection of CHO cells with each reporter plasmid showed that designed and observed activities were highly correlated ($r^2=0.92$; FIG. 5B). At very low-high levels of transcription (5-60 RPU), the in vitro activity of all promoters was within 5 RPU of predicted activities. However, when transcriptional output was very high (80-100 RPU), the difference between observed and predicted activities varied by 10-22 RPU (11-22%). It has previously been shown that transcriptional noise increases concomitantly with both promoter activity and TF binding site copy number (56,57). This may explain why the four strongest promoters (with the largest TFRE copy numbers) exhibited the greatest deviation between observed and predicted activities. However, as all promoters with designed activities ≥80 exhibited activities ≥78 in vitro, it was concluded that very strong promoters can be routinely created in silico, but that at this level of expression, very precise control of transcription may be intractable.

To test the function of the designed sequences in an intragenomic context, CHO cells were stably transfected with synthetic promoter-reporter plasmids coexpressing a glutamine synthetase selection marker gene (58). In order to analyze the full range of transcriptional control, promoters with activities of 5, 10, 20, 80, and 100 RPU were evaluated. Stably transfected CHO cell pools were selected in medium containing methionine sulphoximine and re-adapted to suspension culture. To evaluate promoter performance in an industrially-relevant bioproduction context, promoter activities were measured during a seven-day batch-production process. As shown in FIG. 5C, the promoter activities observed in transient expression systems were maintained in chromosomal contexts. qPCR analysis of SEAP mRNA abundance revealed that the ratio of relative promoter strengths in stable expression systems (100:72:28:16:8) was highly similar to the original designed ratio of promoter activities (100:80:20:10:5). Moreover, relative promoter activities were maintained between exponential (day 4) and stationary (day 7) phases of growth. These data confirm the assumption that promoter activity dynamics can be specifically tailored by designing sequences to bind TFs with synchronous expression profiles. Further, no synthetic promoter had a significant effect on cell growth or viability (viable cell concentration and culture viability varied by less than 20% between all cell pools at days 4 and 7; data not shown), validating the selection of TFRE-combinations that were specifically designed to minimize off-target effects on cellular performance. Finally, to assess gene expression stability, high and low producer stable pools were subcultured in MSX-containing medium for sixty generations. As shown in FIG. 5D, SEAP production was not significantly reduced following long-term culture, confirming that synthetic sequences had been successfully designed to prevent promoter silencing.

Example 6: Conclusion

In conclusion, it has been, for the first time, demonstrated in silico model-directed construction of mammalian promoters that exhibit custom-designed functionalities in vitro. The design process described can be applied to create optimized promoter sequences for any specific host cell-type or gene expression context. The model provided herein explaining heterotypic element activities has higher predictive power than any previously published model of mammalian promoter activity, and provides new insights into eukaryotic transcriptional regulatory mechanisms. This simplified model of promoter regulation described, facilitates the design of promoters entirely in silico from 'OMICS datasets, obviating the requirement for in vitro screening, for example using a detailed understanding of how many discrete TF-TFRE interactions function within the context of heterotypic architectures. Indeed, the combination of modular TFRE blocks for de novo heterotypic promoter design may be particularly applicable when constructing genetic circuits that use multiple synthetic TFs. By demonstrating that promoters can be created in silico according to relatively simple design rules, this study provides new tools for mammalian synthetic biology.

Example 7: Synthetic Promoters Exhibit Predictable Activity in Expression of Recombinant Proteins in Stably Transfected Cell Lines Expression vectors containing hCMV-IE1 and synthetic promoters with three different designed activity levels (RPU100, PRU60, and RPU10) in vector backbone containing the GS selective marker were constructed. The promoters were inserted upstream of an immune activator protein. Each construct was tested in triplicate, and the productivity data was averaged from the three replications. The expression levels were compared in transient transfection (FIG. 7) and stable pool (FIG. 8) in fed-batch conditions. Quantification of the immune activator protein was measured by Octet assay. In the transient transfection experiment, the expression level of the immune activator protein under the control of the RPU100 promoter was increased by 1.33-fold as compared to under the control of hCMV-IE1. The expression level under the control of the RPU60 promoter was not improved, and the expression level under the control of the RPU10 promoter decreased by 6-fold compared to under the control of hCMV-IE1. In the stable pool, the expression level of the immune activator protein gradually increased through day 13. The maximum productivity was 1.8 g/L under the control of the RPU100 promoter. The expression level under the control of the RPU100 promoter was 1.1 fold higher than under the control of hCMV-IE1, whereas under the controls of the RPU60 and RPU10 promoters was decreased by 2.8-fold and 18-fold, respectively, compared to hCMV-IE1. These results demonstrate that expression levels can be altered using promoters designed to have different strengths, and they show consistency in both transient transfection and stable pools. Titers were 1.51×, 1.56×, and 1.1× higher on days 9, 11, and 13, respectively, when using synthetic promoter RPU100 as compared to hCMV-IE1. Given the significantly increased titers on days 9 and 11, the RPU100 promoter can facilitate the use of a shorter production process.

Additional consistency was demonstrated by testing synthetic promoters with the following TFREs a different host cell, CHO-S:
100RPU Construct A:
(GC-box)-(ARE)-(NFkB-RE)-(DRE)-(EBS1)-(ARE)-(DRE)-(NFkB-RE)-(GC-box)-(NFkB-RE)-(ARE)
100RPU Construct B:
(NFkB-RE)-(DRE)-(GC-box)-(ARE)-(NFkB-RE)-(C/EBP-RE)-(DRE)-(NFkB-RE)-(EBS1)-(NFkB-RE)-(ARE)

The activity of the tested promoters was maintained in CHO-S cells.

The productivity gains facilitated by using 100RPU, relative to hCMV-IE1, were reduced in this specific expression context (compared to the effects seen in the production of SEAP). This could have been caused by the specific recombinant protein, production process, or vector utilized. Indeed, the relative increases in productivity (compared to hCMV-IE1) and the exact ratio of expression levels enabled by synthetic promoters will vary in different contexts. However, these results emphasize the robustness of synthetic promoter function, where testing a minimal number of constructs enabled both significant increases in yield (compared to hCMV-IE1), and predictable titratable control of protein expression, in a substantially different expression context. Even in situations where synthetic promoters do not offer significant productivity gains relative to hCMV-IE1, their use may still be preferable as i) they have been designed to minimize promoter silencing, and ii) they are significantly reduced in size.

REFERENCES

1. Mutalik, V. K., Guimaraes, J. C., Cambray, G., Lam, C., Christoffersen, M. J., Mai, Q.-A., Tran, A. B., Paull, M., Keasling, J. D. and Arkin, A. P. (2013) Precise and reliable gene expression via standard transcription and translation initiation elements. *Nat. Methods,* 10, 354-360.
2. Brewster, R. C., Weinert, F. M., Garcia, H. G., Song, D., Rydenfelt, M. and Phillips, R. (2014) The transcription factor titration effect dictates level of gene expression. *Cell,* 156, 1312-1323.
3. Karreth, F. A., Tay, Y. and Pandolfi, P. P. (2014) Target competition: transcription factors enter the limelight. *Genome Biol.,* 15, 114.
4. Fan, L., Kadura, I., Krebs, L. E., Larson, J. L., Bowden, D. M. and Frye, C. C. (2013) Development of a highly-efficient CHO cell line generation system with engineered SV40E promoter. *J. Biotechnol.,* 168, 652-658.
5. Chen, J., Haverty, J., Deng, L., Li, G., Qiu, P., Liu, Z. and Shi, S. (2013) Identification of a novel endogenous regulatory element in Chinese hamster ovary cells by promoter trap. *J. Biotechnol.,* 167, 255-261.
6. Sumitomo, Y., Higashitsuji, H., Higashitsuji, H., Liu, Y., Fujita, T., Sakurai, T., Candeias, M. M., Itoh, K., Chiba, T. and Fujita, J. (2012) Identification of a novel enhancer that binds Sp1 and contributes to induction of cold-inducible RNA-binding protein (cirp) expression in mammalian cells. *BMC Biotechnol.,* 12, 72.
7. Mariati, Yeo, J. H., Koh, E. Y., Ho, S. C. and Yang, Y. (2014) Insertion of core CpG island element into human CMV promoter for enhancing recombinant protein expression stability in CHO cells. *Biotechnol. Prog.,* 30, 523-534.
8. Ferreira, J. P., Peacock, R. W., Lawhorn, I. E. and Wang, C. L. (2011) Modulating ectopic gene expression levels by using retroviral vectors equipped with synthetic promoters. *Syst. Synth. Biol.,* 5, 131-138.
9. Kwasnieski, J. C., Mogno, I., Myers, C. A., Corbo, J. C. and Cohen, B. A. (2012) Complex effects of nucleotide variants in a mammalian cis-regulatory element. *Proc. Natl. Acad. Sci.,* 109, 19498-19503.
10. Brown, A. J. and James, D. C. (2015) Precision control of recombinant gene transcription for CHO cell synthetic biology. *Biotechnol. Adv.,* 34(5), 492-503
11. Gaj, T., Gersbach, C. A. and Barbas, C. F. (2013) ZFN, TALEN, and CRISPR/Cas-based methods for genome engineering. *Trends Biotechnol.,* 31, 397-405.
12. Perez-Pinera, P., Ousterout, D. G., Brunger, J. M., Farin, A. M., Glass, K. A., Guilak, F., Crawford, G. E., Hartemink, A. J. and Gersbach, C. A. (2013) Synergistic and tunable human gene activation by combinations of synthetic transcription factors. *Nat. Methods,* 10, 239-242.
13. Rössger, K., Charpin-El-Hamri, G. and Fussenegger, M. (2014) Bile acid-controlled transgene expression in mammalian cells and mice. *Metab. Eng.,* 21, 81-90.
14. Chavez, A., Scheiman, J., Vora, S., Pruitt, B. W., Tuttle, M., Iyer, E. P., Lin, S., Kiani, S., Guzman, C. D. and Wiegand, D. J. (2015) Highly efficient Cas9-mediated transcriptional programming. *Nat. Methods,* 12, 326-328.
15. Hansen, A. S. and O'Shea, E. K. (2013) Promoter decoding of transcription factor dynamics involves a trade-off between noise and control of gene expression. *Mol. Syst. Biol.,* 9, 704.
16. Sharon, E., Kalma, Y., Sharp, A., Raveh-Sadka, T., Levo, M., Zeevi, D., Keren, L., Yakhini, Z., Weinberger, A. and Segal, E. (2012) Inferring gene regulatory logic from high-throughput measurements of thousands of systematically designed promoters. *Nat. Biotechnol.,* 30, 521-530.
17. Weingarten-Gabbay, S. and Segal, E. (2014) The grammar of transcriptional regulation. *Hum. Genet.,* 133, 701-711.
18. Smith, R. P., Taher, L., Patwardhan, R. P., Kim, M. J., Inoue, F., Shendure, J., Ovcharenko, I. and Ahituv, N. (2013) Massively parallel decoding of mammalian regulatory sequences supports a flexible organizational model. *Nat. Genet.,* 45, 1021-1028.
19. Arnosti, D. N. and Kulkarni, M. M. (2005) Transcriptional enhancers: Intelligent enhanceosomes or flexible billboards? *J. Cell. Biochem.,* 94, 890-898.
20. Rastegar, S., Hess, I., Dickmeis, T., Nicod, J. C., Ertzer, R., Hadzhiev, Y., Thies, W.-G., Scherer, G. and Strähle, U. (2008) The words of the regulatory code are arranged in a variable manner in highly conserved enhancers. *Dev. Biol.,* 318, 366-377.
21. Ravasi, T., Suzuki, H., Cannistraci, C. V., Katayama, S., Bajic, V. B., Tan, K., Akalin, A., Schmeier, S., Kanamori-Katayama, M. and Bertin, N. (2010) An atlas of combinatorial transcriptional regulation in mouse and man. *Cell,* 140, 744-752.
22. Gertz, J. and Cohen, B. A. (2009) Environment-specific combinatorial cis-regulation in synthetic promoters. *Mol. Syst. Biol.,* 5, 244.
23. Segal, E., Raveh-Sadka, T., Schroeder, M., Unnerstall, U. and Gaul, U. (2008) Predicting expression patterns from regulatory sequence in Drosophila segmentation. *Nature,* 451, 535-540.
24. Trapnell, C., Pachter, L. and Salzberg, S. L. (2009) TopHat: discovering splice junctions with RNA-Seq. *Bioinformatics,* 25, 1105-1111.
25. Xu, X., Nagarajan, H., Lewis, N. E., Pan, S., Cai, Z., Liu, X., Chen, W., Xie, M., Wang, W. and Hammond, S. (2011) The genomic sequence of the Chinese hamster ovary (CHO)-K1 cell line. *Nat. Biotechnol.,* 29, 735-741.
26. Trapnell, C., Williams, B. A., Pertea, G., Mortazavi, A., Kwan, G., Van Baren, M. J., Salzberg, S. L., Wold, B. J. and Pachter, L. (2010) Transcript assembly and quantification by RNA-Seq reveals unannotated transcripts and isoform switching during cell differentiation. *Nat. Biotechnol.,* 28, 511-515.
27. Chawla, K., Tripathi, S., Thommesen, L., Lægreid, A. and Kuiper, M. (2013) TFcheckpoint: a curated compendium of specific DNA-binding RNA polymerase II transcription factors. *Bioinformatics,* 29(19), 2519-20.
28. Tripathi, S., Vercruysse, S., Chawla, K., Christie, K. R., Blake, J. A., Huntley, R. P., Orchard, S., Hermjakob, H., Thommesen, L. and Lægreid, A. (2016) Gene regulation knowledge commons: community action takes care of DNA binding transcription factors. *Database,* 2016, baw088.
29. Mathelier, A., Zhao, X., Zhang, A. W., Parcy, F., Worsley-Hunt, R., Arenillas, D. J., Buchman, S., Chen, C.-y., Chou, A. and Ienasescu, H. (2013) JASPAR 2014: an extensively expanded and updated open-access database of transcription factor binding profiles. *Nucleic Acids Res.,* gkt997.
30. Brown, A. J., Mainwaring, D. O., Sweeney, B. and James, D. C. (2013) Block decoys: transcription-factor decoys designed for in vitro gene regulation studies. *Anal. Biochem.,* 443, 205-210.
31. Brown, A. J., Sweeney, B., Mainwaring, D. O. and James, D. C. (2014) Synthetic promoters for CHO cell engineering. *Biotechnol. Bioeng.,* 111, 1638-1647.
32. Senthilkumar, R., Sabarinathan, R., Hameed, B. S., Banerjee, N., Chidambarathanu, N., Karthik, R. and Sekar, K. (2010) FAIR: A server for internal sequence repeats. *Bioinformation,* 4, 271.

33. Manke, T., Roider, H. G. and Vingron, M. (2008) Statistical modeling of transcription factor binding affinities predicts regulatory interactions. *PLoS Comput. Biol.,* 4, e1000039.
34. Cartharius, K., Frech, K., Grote, K., Klocke, B., Haltmeier, M., Klingenhoff, A., Frisch, M., Bayerlein, M. and Werner, T. (2005) MatInspector and beyond: promoter analysis based on transcription factor binding sites. *Bioinformatics,* 21, 2933-2942.
35. Kim, M., O'Callaghan, P. M., Droms, K. A. and James, D. C. (2011) A mechanistic understanding of production instability in CHO cell lines expressing recombinant monoclonal antibodies. *Biotechnol. Bioeng.,* 108, 2434-2446.
36. Dahodwala, H. and Sharfstein, S. T. (2014) Role of epigenetics in expression of recombinant proteins from mammalian cells. *Pharm. Bioprocess.,* 2, 403-419.
37. Gertz, J., Siggia, E. D. and Cohen, B. A. (2009) Analysis of combinatorial cis-regulation in synthetic and genomic promoters. *Nature,* 457, 215-218.
38. Sheng, X., Wu, J., Sun, Q., Li, X., Xian, F., Sun, M., Fang, W., Chen, M., Yu, J. and Xiao, J. (2016) MTD: a mammalian transcriptomic database to explore gene expression and regulation. *Brief Bioinform.,* 18(1), 28-36.
39. Vaquerizas, J. M., Kummerfeld, S. K., Teichmann, S. A. and Luscombe, N. M. (2009) A census of human transcription factors: function, expression and evolution. *Nat. Rev. Genet.,* 10, 252-263.
40. Tripathi, S., Christie, K. R., Balakrishnan, R., Huntley, R., Hill, D. P., Thommesen, L., Blake, J. A., Kuiper, M. and Lægreid, A. (2013) Gene Ontology annotation of sequence-specific DNA binding transcription factors: setting the stage for a large-scale curation effort. *Database,* 2013, bat062.
41. van Dijk, D., Sharon, E., Lotan-Pompan, M., Weinberger, A., Segal, E. and Carey, L. B. (2017) Large-scale mapping of gene regulatory logic reveals context-dependent repression by transcriptional activators. *Genome Res.,* 27, 87-94.
42. Wajapeyee, N., Malonia, S. K., Palakurthy, R. K. and Green, M. R. (2013) Oncogenic RAS directs silencing of tumor suppressor genes through ordered recruitment of transcriptional repressors. *Genes Dev.,* 27, 2221-2226.
43. Smith, Z. D. and Meissner, A. (2013) DNA methylation: roles in mammalian development. *Nat. Rev. Genet.,* 14, 204-220.
44. Grskovic, M., Chaivorapol, C., Gaspar-Maia, A., Li, H. and Ramalho-Santos, M. (2007) Systematic identification of cis-regulatory sequences active in mouse and human embryonic stem cells. *PLoS Genet.,* 3, e145.
45. Giniger, E. and Ptashne, M. (1988) Cooperative DNA binding of the yeast transcriptional activator GAL4. *Proc. Natl. Acad. Sci.,* 85, 382-386.
46. Hussain, H., Maldonado-Agurto, R. and Dickson, A. J. (2014) The endoplasmic reticulum and unfolded protein response in the control of mammalian recombinant protein production. *Biotechnol. Lett.,* 36, 1581-1593.
47. Gorman, A. M., Healy, S. J., Jager, R. and Samali, A. (2012) Stress management at the ER: regulators of ER stress-induced apoptosis. *Pharmacol. Ther.,* 134, 306-316.
48. Sano, R. and Reed, J. C. (2013) ER stress-induced cell death mechanisms. *BBA-Mol. Cell Res.,* 1833, 3460-3470.
49. Yang, Y., Chusainow, J. and Yap, M. G. (2010) DNA methylation contributes to loss in productivity of monoclonal antibody-producing CHO cell lines. *J. Biotechnol.,* 147, 180-185.
50. Moynahan, M. E. and Jasin, M. (2010) Mitotic homologous recombination maintains genomic stability and suppresses tumorigenesis. *Nat. rev. Mol. cell biol.,* 11, 196-207.
51. Jasin, M. and Rothstein, R. (2013) Repair of strand breaks by homologous recombination. *Cold Spring Harb. Perspect. Biol.,* 5, a012740.
52. Baudin, A., Ozier-Kalogeropoulos, O., Denouel, A., Lacroute, F. and Cullin, C. (1993) A simple and efficient method for direct gene deletion in *Saccharomyces cerevisiae. Nucleic Acids Res.,* 21, 3329.
53. Sleight, S. C., Bartley, B. A., Lieviant, J. A. and Sauro, H. M. (2010) Designing and engineering evolutionary robust genetic circuits. *J. Biol. Eng.,* 4, 12.
54. Lambert, S., Saintigny, Y., Delacote, F., Amiot, F., Chaput, B., Lecomte, M., Huck, S., Bertrand, P. and Lopez, B. (1999) Analysis of intrachromosomal homologous recombination in mammalian cell, using tandem repeat sequences. *Mutat. Res., DNA Repair,* 433, 159-168.
55. Read, L. R., Raynard, S. J., Rukść, A. and Baker, M. D. (2004) Gene repeat expansion and contraction by spontaneous intrachromosomal homologous recombination in mammalian cells. *Nucleic Acids Res.,* 32, 1184-1196.
56. Sharon, E., van Dijk, D., Kalma, Y., Keren, L., Manor, O., Yakhini, Z and Segal, E. (2014) Probing the effect of promoters on noise in gene expression using thousands of designed sequences. *Genome Res.,* 24, 1698-1706.
57. Murphy, K. F., Balázsi, G. and Collins, J. J. (2007) Combinatorial promoter design for engineering noisy gene expression. *Proc. Natl. Acad. Sci.,* 104, 12726-12731.
58. Cockett, M., Bebbington, C. and Yarranton, G. (1990) High level expression of tissue inhibitor of metalloproteinases in Chinese hamster ovary cells using glutamine synthetase gene amplification. *Nat. Biotechnol.,* 8, 662-667.

What is claimed is:

1. A synthetic promoter comprising (a) a nucleotide sequence comprising 4 to 20 transcription factor regulatory elements (TFREs) and (b) a promoter core, wherein the nucleotide sequence comprising the TRFEs is located on upstream of the promoter core, wherein at least one third of the TFREs are individually selected from the group consisting of antioxidant RE (ARE), ETS binding site 1 (EBS1), endoplasmic reticulum stress RE (ERSE), and dioxin RE (DRE) TFREs, and wherein the promoter core comprises SEQ ID NO: 37.

* * * * *

SEQUENCE LISTING

<160> NUMBER OF SEQ ID NOS: 50

<210> SEQ ID NO 1
<211> LENGTH: 6
<212> TYPE: DNA
<213> ORGANISM: Artificial Sequence
<220> FEATURE:
<223> OTHER INFORMATION: Enhancer box (E-box)

```
<400> SEQUENCE: 1 cacgtg                                                                6

<210> SEQ ID NO 2
<211> LENGTH: 8
<212> TYPE: DNA
<213> ORGANISM: Artificial Sequence
<220> FEATURE:
<223> OTHER INFORMATION: cAMP RE (CRE)

<400> SEQUENCE: 2 tgacgtca                                                              8

<210> SEQ ID NO 3
<211> LENGTH: 9
<212> TYPE: DNA
<213> ORGANISM: Artificial Sequence
<220> FEATURE:
<223> OTHER INFORMATION: Amino acid RE (AARE)

<400> SEQUENCE: 3 attgcatca                                                             9

<210> SEQ ID NO 4
<211> LENGTH: 8
<212> TYPE: DNA
<213> ORGANISM: Artificial Sequence
<220> FEATURE:
<223> OTHER INFORMATION: Forkhead box binding site (FBS)

<400> SEQUENCE: 4 ataaacaa                                                              8

<210> SEQ ID NO 5
<211> LENGTH: 10
<212> TYPE: DNA
<213> ORGANISM: Artificial Sequence
<220> FEATURE:
<223> OTHER INFORMATION: Nuclear factor kappa B (NFkB-RE)

<400> SEQUENCE: 5
gggactttcc                                                           10

<210> SEQ ID NO 6
<211> LENGTH: 15
<212> TYPE: DNA
<213> ORGANISM: Artificial Sequence
<220> FEATURE:
<223> OTHER INFORMATION: Nuclear factor 1 RE (NF1-RE)

<400> SEQUENCE: 6
ttggctatat gccaa                                                     15

<210> SEQ ID NO 7
<211> LENGTH: 13
<212> TYPE: DNA
<213> ORGANISM: Artificial Sequence
<220> FEATURE:
<223> OTHER INFORMATION: Antioxidant RE (ARE)

<400> SEQUENCE: 7
atgacacagc aat                                                       13
```

```
<210> SEQ ID NO 8
<211> LENGTH: 8
<212> TYPE: DNA
<213> ORGANISM: Artificial Sequence
<220> FEATURE:
<223> OTHER INFORMATION: Elongation factor 2 RE (E2F-RE)

<400> SEQUENCE: 8 tttcgcgc                                                                        8

<210> SEQ ID NO 9
<211> LENGTH: 9
<212> TYPE: DNA
<213> ORGANISM: Artificial Sequence
<220> FEATURE:
<223> OTHER INFORMATION: GC-box

<400> SEQUENCE: 9 ggggcgggg                                                                       9

<210> SEQ ID NO 10
<211> LENGTH: 9
<212> TYPE: DNA
<213> ORGANISM: Artificial Sequence
<220> FEATURE:
<223> OTHER INFORMATION: ETS binding site 1 (EBS1)

<400> SEQUENCE: 10 accggaagt                                                                       9

<210> SEQ ID NO 11
<211> LENGTH: 9
<212> TYPE: DNA
<213> ORGANISM: Artificial Sequence
<220> FEATURE:
<223> OTHER INFORMATION: ETS binding site 2 (EBS2)

<400> SEQUENCE: 11 acaggaagt                                                                       9

<210> SEQ ID NO 12
<211> LENGTH: 21
<212> TYPE: DNA
<213> ORGANISM: Artificial Sequence
<220> FEATURE:
<223> OTHER INFORMATION: Unfolded protein response element (UPRE)

<400> SEQUENCE: 12
gctgacgtgg tgctgacgtg g                                                        21

<210> SEQ ID NO 13
<211> LENGTH: 11
<212> TYPE: DNA
<213> ORGANISM: Artificial Sequence
<220> FEATURE:
<223> OTHER INFORMATION: Endoplasmic reticulum stress RE II (ERSE-II)

<400> SEQUENCE: 13
attggtccac g                                                                   11

<210> SEQ ID NO 14
<211> LENGTH: 9
<212> TYPE: DNA
<213> ORGANISM: Artificial Sequence
<220> FEATURE:
<223> OTHER INFORMATION: Yin Yang 1 RE (YY1-RE)
```

```
<400> SEQUENCE: 14 cgccatttt                                                                9

<210> SEQ ID NO 15
<211> LENGTH: 19
<212> TYPE: DNA
<213> ORGANISM: Artificial Sequence
<220> FEATURE:
<223> OTHER INFORMATION: Endoplasmic reticulum stress RE (ERSE)

<400> SEQUENCE: 15
ccaatggcca gcctccacg                                                    19

<210> SEQ ID NO 16
<211> LENGTH: 10
<212> TYPE: DNA
<213> ORGANISM: Artificial Sequence
<220> FEATURE:
<223> OTHER INFORMATION: Sterol RE (SRE)

<400> SEQUENCE: 16
atcaccccac                                                              10

<210> SEQ ID NO 17
<211> LENGTH: 13
<212> TYPE: DNA
<213> ORGANISM: Artificial Sequence
<220> FEATURE:
<223> OTHER INFORMATION: Peroxisome proliferator RE (PPRE)

<400> SEQUENCE: 17
aggtcaaagg tca                                                          13

<210> SEQ ID NO 18
<211> LENGTH: 9
<212> TYPE: DNA
<213> ORGANISM: Artificial Sequence
<220> FEATURE:
<223> OTHER INFORMATION: Signal transducer and activator of
      transcription RE (STAT-RE)

<400> SEQUENCE: 18 ttccaggaa                                                                9

<210> SEQ ID NO 19
<211> LENGTH: 8
<212> TYPE: DNA
<213> ORGANISM: Artificial Sequence
<220> FEATURE:
<223> OTHER INFORMATION: CACCC-box

<400> SEQUENCE: 19 ccacaccc                                                                 8

<210> SEQ ID NO 20
<211> LENGTH: 10
<212> TYPE: DNA
<213> ORGANISM: Artificial Sequence
<220> FEATURE:
<223> OTHER INFORMATION: SMAD binding element (SBE)

<400> SEQUENCE: 20
gtctgcagac                                                              10
```

```
<210> SEQ ID NO 21
<211> LENGTH: 16
<212> TYPE: DNA
<213> ORGANISM: Artificial Sequence
<220> FEATURE:
<223> OTHER INFORMATION: Thyroid response element 1 (TRE1)

<400> SEQUENCE: 21
aggtcacttc aggtca                                                   16

<210> SEQ ID NO 22
<211> LENGTH: 18
<212> TYPE: DNA
<213> ORGANISM: Artificial Sequence
<220> FEATURE:
<223> OTHER INFORMATION: Thyroid response element 2 (TRE2)

<400> SEQUENCE: 22
tgaccttggc ataggtca                                                 18

<210> SEQ ID NO 23
<211> LENGTH: 8
<212> TYPE: DNA
<213> ORGANISM: Artificial Sequence
<220> FEATURE:
<223> OTHER INFORMATION: CCAAT-enhancer binding protein RE (C/EBP-RE)

<400> SEQUENCE: 23 ttgcgcaa                                                             8

<210> SEQ ID NO 24
<211> LENGTH: 9
<212> TYPE: DNA
<213> ORGANISM: Artificial Sequence
<220> FEATURE:
<223> OTHER INFORMATION: MCAT

<400> SEQUENCE: 24 acattcctg                                                            9

<210> SEQ ID NO 25
<211> LENGTH: 6
<212> TYPE: DNA
<213> ORGANISM: Artificial Sequence
<220> FEATURE:
<223> OTHER INFORMATION: Cellular myeloblastosis RE (cMyb-RE)

<400> SEQUENCE: 25 taacgg                                                               6

<210> SEQ ID NO 26
<211> LENGTH: 14
<212> TYPE: DNA
<213> ORGANISM: Artificial Sequence
<220> FEATURE:
<223> OTHER INFORMATION: Heat shock element (HSE)

<400> SEQUENCE: 26
agaacattct agaa                                                     14

<210> SEQ ID NO 27
<211> LENGTH: 15
<212> TYPE: DNA
<213> ORGANISM: Artificial Sequence
<220> FEATURE:
<223> OTHER INFORMATION: Estrogen-related receptor RE (ERRE)
```

```
<400> SEQUENCE: 27
aggtcatttt gacct                                                     15

<210> SEQ ID NO 28
<211> LENGTH: 11
<212> TYPE: DNA
<213> ORGANISM: Artificial Sequence
<220> FEATURE:
<223> OTHER INFORMATION: Metal RE (MRE)

<400> SEQUENCE: 28
tgcacacagc c                                                         11

<210> SEQ ID NO 29
<211> LENGTH: 10
<212> TYPE: DNA
<213> ORGANISM: Artificial Sequence
<220> FEATURE:
<223> OTHER INFORMATION: D-box

<400> SEQUENCE: 29
attatgtaac                                                           10

<210> SEQ ID NO 30
<211> LENGTH: 8
<212> TYPE: DNA
<213> ORGANISM: Artificial Sequence
<220> FEATURE:
<223> OTHER INFORMATION: Hypoxia RE (HRE)

<400> SEQUENCE: 30 gtacgtgc                                                              8

<210> SEQ ID NO 31
<211> LENGTH: 14
<212> TYPE: DNA
<213> ORGANISM: Artificial Sequence
<220> FEATURE:
<223> OTHER INFORMATION: Dioxin RE (DRE)

<400> SEQUENCE: 31
gcttgcgtga gaag                                                      14

<210> SEQ ID NO 32
<211> LENGTH: 10
<212> TYPE: DNA
<213> ORGANISM: Artificial Sequence
<220> FEATURE:
<223> OTHER INFORMATION: CC(A/T)6GG element (CArG)

<400> SEQUENCE: 32
ccaaatttgg                                                           10

<210> SEQ ID NO 33
<211> LENGTH: 84
<212> TYPE: DNA
<213> ORGANISM: Artificial Sequence
<220> FEATURE:
<223> OTHER INFORMATION: A minimal CMV core promoter

<400> SEQUENCE: 33
aggtctatat aagcagagct cgtttagtga accgtcagat cgcctagata cgccatccac    60
gctgttttga cctccataga agac                                           84
```

```
<210> SEQ ID NO 34
<211> LENGTH: 43
<212> TYPE: DNA
<213> ORGANISM: Artificial Sequence
<220> FEATURE:
<223> OTHER INFORMATION: Gnb1

<400> SEQUENCE: 34
ccatatgttt ctttcccaat ggcaagtcgt cgtacccagc aag                    43

<210> SEQ ID NO 35
<211> LENGTH: 42
<212> TYPE: DNA
<213> ORGANISM: Artificial Sequence
<220> FEATURE:
<223> OTHER INFORMATION: Fkbp1a

<400> SEQUENCE: 35
ctctcgggac agaaacaagc gacctacact catctgggct ac                     42

<210> SEQ ID NO 36
<211> LENGTH: 40
<212> TYPE: DNA
<213> ORGANISM: Artificial Sequence
<220> FEATURE:
<223> OTHER INFORMATION: Seap

<400> SEQUENCE: 36
gaatcgggcc aagaaagcag atgagctgcg tagcgatgtc                        40

<210> SEQ ID NO 37
<211> LENGTH: 102
<212> TYPE: DNA
<213> ORGANISM: Artificial Sequence
<220> FEATURE:
<223> OTHER INFORMATION: 5 RPU construct 1

<400> SEQUENCE: 37
tataggaagg tcttaccgga agttccttag ctgatagtat accagatttt ttgcgcaatt  60
ctagactgat catctaacga cctattaccg gaagttagta tg                     102

<210> SEQ ID NO 38
<211> LENGTH: 101
<212> TYPE: DNA
<213> ORGANISM: Artificial Sequence
<220> FEATURE:
<223> OTHER INFORMATION: 5 RPU construct 2

<400> SEQUENCE: 38
aaggtcctga tatggggcgg ggactagaca gtatggttag agacctatta ccggaagttc  60
cttaggtata ctctaaccag atttttgcg caatttgatc a                       101

<210> SEQ ID NO 39
<211> LENGTH: 106
<212> TYPE: DNA
<213> ORGANISM: Artificial Sequence
<220> FEATURE:
<223> OTHER INFORMATION: 10 RPU construct 1

<400> SEQUENCE: 39
tggggcgggg agtatacgac ctattttgcg caattctgat aaaggtctta ccggaagttc  60
agatttatag gttttgcgca attagtatgc cttagtgggg cgggga                 106
```

```
<210> SEQ ID NO 40
<211> LENGTH: 107
<212> TYPE: DNA
<213> ORGANISM: Artificial Sequence
<220> FEATURE:
<223> OTHER INFORMATION: 10 RPU construct 2

<400> SEQUENCE: 40
ttaccggaag ttaaggtctt ttgcgcaatt cagattgacc tattaccgga agtttatagg      60
tggggcgggg agttagattt tgcgcaattt gatcattacc ggaagtt                  107

<210> SEQ ID NO 41
<211> LENGTH: 106
<212> TYPE: DNA
<213> ORGANISM: Artificial Sequence
<220> FEATURE:
<223> OTHER INFORMATION: 20 RPU construct 1

<400> SEQUENCE: 41
ttaccggaag ttgacctatg cttgcgtgag aagagttaga tggggcgggg aaaggtcttt      60
tgcgcaattc agattttacc ggaagtttat aggatgacac agcaat                   106

<210> SEQ ID NO 42
<211> LENGTH: 118
<212> TYPE: DNA
<213> ORGANISM: Artificial Sequence
<220> FEATURE:
<223> OTHER INFORMATION: 20 RPU construct 2

<400> SEQUENCE: 42
tggggcgggg acagatttta ccggaagttt ataggttttg cgcaattagt atgtggggcg      60
gggatctaac atgacacagc aataaggtct taccggaagt tgacctatgg ggcgggga      118

<210> SEQ ID NO 43
<211> LENGTH: 125
<212> TYPE: DNA
<213> ORGANISM: Artificial Sequence
<220> FEATURE:
<223> OTHER INFORMATION: 40 RPU construct 1

<400> SEQUENCE: 43
ttttgcgcaa tttataggtg gggcggggaa aggtcatgac acagcaatca gatttgcttg      60
cgtgagaaga agtatgttac cggaagttga cctatgggac tttccatcta acatgacaca    120
gcaat                                                                125

<210> SEQ ID NO 44
<211> LENGTH: 146
<212> TYPE: DNA
<213> ORGANISM: Artificial Sequence
<220> FEATURE:
<223> OTHER INFORMATION: 40 RPU construct 2

<400> SEQUENCE: 44
ttaccggaag ttccttagtg cttgcgtgag aagagtatac tggggcgggg actagactta      60
ccggaagttt gatcaatgac acagcaatag tatgtgcttg cgtgagaaga gacctatggg    120
actttccacc ttagttaccg gaagtt                                         146

<210> SEQ ID NO 45
<211> LENGTH: 183
<212> TYPE: DNA
<213> ORGANISM: Artificial Sequence
```

```
<220> FEATURE:
<223> OTHER INFORMATION: 60 RPU construct 1

<400> SEQUENCE: 45
ttaccggaag ttctagactg cttgcgtgag aagagaccta atgacacagc aattctaact    60
ggggcgggga gtatactggg actttccatg atcattaccg aagttcaga ttttttgcgc   120 aatttatagg tgcttgcgtg agaagaaagg tctgggactt tccaagtatg atgacacagc   180
aat                                                                 183

<210> SEQ ID NO 46
<211> LENGTH: 176
<212> TYPE: DNA
<213> ORGANISM: Artificial Sequence
<220> FEATURE:
<223> OTHER INFORMATION: 60 RPU construct 2

<400> SEQUENCE: 46
tggggcgggg agttagatgg gactttccac agatttacc ggaagttctg atatggggcg     60
gggagtatac tgcttgcgtg agaagatata ggtgggactt ccaccttag tggggcgggg   120 actagacatg acacagcaat tctaacttac cggaagtttg atcatgggac tttcca        176

<210> SEQ ID NO 47
<211> LENGTH: 201
<212> TYPE: DNA
<213> ORGANISM: Artificial Sequence
<220> FEATURE:
<223> OTHER INFORMATION: 80 RPU construct 1

<400> SEQUENCE: 47
tggggcgggg aagtatgatg acacagcaat tgatcatggg actttccact agactgcttg     60
cgtgagaaga aaggtcttac cggaagttga cctaatgaca cagcaatgtt agatgcttgc   120
gtgagaagac tgatatggga ctttccagta tactggggcg gggatctaac tgggactttc   180
cacagattat gacacagcaa t                                              201

<210> SEQ ID NO 48
<211> LENGTH: 201
<212> TYPE: DNA
<213> ORGANISM: Artificial Sequence
<220> FEATURE:
<223> OTHER INFORMATION: 80 RPU construct 2

<400> SEQUENCE: 48
tgggactttc caagtatgtg cttgcgtgag aagagaccta tggggcgggg atctaacatg     60
acacagcaat cagatttggg actttccaaa ggtcttttgc gcaattctga tatgcttgcg   120
tgagaagagt atactgggac tttccacctt agttaccgga agtttatagg tgggactttc   180
cactagacat gacacagcaa t                                              201

<210> SEQ ID NO 49
<211> LENGTH: 266
<212> TYPE: DNA
<213> ORGANISM: Artificial Sequence
<220> FEATURE:
<223> OTHER INFORMATION: 100 RPU construct 1

<400> SEQUENCE: 49
tgggactttc cactagacat gacacagcaa tctgatatgc ttgcgtgaga agaggattca     60
tatcctggga ctttccacag attttaccgg aagttgttag atgcttgcgt gagaagatct   120
```

```
aacatgacac agcaatcctt agtgggactt tccaagtatg tggggcgggg agtatacatg    180
acacagcaat tgatcattac cggaagttta taggtgggac tttccagacc tatgcttgcg    240
tgagaagaaa ggtctgggac tttcca                                         266

<210> SEQ ID NO 50
<211> LENGTH: 263
<212> TYPE: DNA
<213> ORGANISM: Artificial Sequence
<220> FEATURE:
<223> OTHER INFORMATION: 100 RPU construct 2

<400> SEQUENCE: 50
tgggactttc cacctagat gacacagcaa tcagatttgc ttgcgtgaga agatatagga     60
tgacacagca atctagactg ggactttcca ctgatatttt gcgcaattga cctaatgaca   120
cagcaatagt atgtggggcg gggatctaac tgggactttc caaaggtctt accggaagtt   180
gttagaatga cacagcaatg gattcatatc ctgggacttt ccagtatact gcttgcgtga   240
gaagatgatc atgggactt cca                                           263
```